(12) United States Patent
Rezaie et al.

(10) Patent No.: US 7,785,857 B2
(45) Date of Patent: Aug. 31, 2010

(54) PROTEIN C VARIANT

(75) Inventors: Alireza R. Rezaie, Eureka, MO (US);
Likui Yang, St. Louis, MO (US)

(73) Assignee: Saint Louis University, Saint Louis, MO (US)

( * ) Notice: Subject to any disclaimer, the term of this patent is extended or adjusted under 35 U.S.C. 154(b) by 312 days.

(21) Appl. No.: 11/848,080

(22) Filed: Aug. 30, 2007

(65) Prior Publication Data

US 2008/0058265 A1 Mar. 6, 2008

Related U.S. Application Data

(60) Provisional application No. 60/841,384, filed on Aug. 31, 2006.

(51) Int. Cl.
*C12N 9/64* (2006.01)
(52) U.S. Cl. .................................................. 435/226
(58) Field of Classification Search ........................ None
See application file for complete search history.

(56) References Cited

U.S. PATENT DOCUMENTS

| 5,084,274 | A | 1/1992 | Griffin et al. |
| 5,516,650 | A | 5/1996 | Foster et al. |
| 6,037,322 | A | 3/2000 | Grinnell et al. |
| 6,156,734 | A | 12/2000 | Grinnell et al. |
| 6,268,337 | B1 | 7/2001 | Grinnell et al. |
| 6,864,237 | B2 | 3/2005 | Wang |
| 7,074,402 | B2 | 7/2006 | Griffin |

OTHER PUBLICATIONS

Bae et al., Engineering a Disulfide Bond to Stabilize the Calcium-binding Loop of Activated Protein C Eliminates Its Anticoagulant but Not Its Protective Signaling Properties, The Journal of Biological Chemistry, 2007; vol. 282, No. 12, pp. 9251-9259.
Bernard et al., Efficacy and safety of recombinant human activated protein C for severe sepsis. N Eng J Med. 2001; 344:699-709.
Bode and Schwager, The refined crystal structure of bovine beta-trypsin at 1.8 Å resolution. II. Crystallographic refinement, calcium binding site, benzamidine binding site and active site at pH 7:0. J Mol Biol. 1975; 98:693-717.
Bode et al., The refined 1.9 Å crystal structure of human thrombin: interaction with D-Phe-Pro-Arg chloromethylketone and significance of the Tyr-Pro-Pro-Trp insertion segment. EMBO J. 1989; 8:3467-3475.
Cheng et al., Activated protein C blocks p53-mediated apoptosis in ischemic human brain endothelium and is neuroprotective. Nature Med. 2003; 9:338-342.
Dang and Di, Residue 225 determines the Na+-induced allosteric regulation of catalytic activity in serine proteases. Proc Natl Acad Sci. (USA), 1996; 93:10653-10656.
Esmon. Molecular events that control the protein C anticoagulant pathway. Thromb. Haemost. 1993; 70:1-5.
Feistritzer and Riewald, Endothelial barrier protection by activated protein C through PAR1-dependent sphingosine 1-phosphate receptor-1 crossactivation. Blood. 2005; 105:3178-3184.

Finigan et al., Activated protein C mediates novel lung endothelial barrier enhancement. The Journal of Biological Chemistry, 2005; 280:17286-17293.
Friedrich et al., Secondary substrate-binding exosite in the serine protease domain of activated protein C important for cleavage at Arg-506 but not at Arg-306 in factor Va. The Journal of Biological Chemistry, 2001; 276:23105-23108.
Gale et al., Molecular Characterization of an Extended Binding Site for Coagulation Factor Va in the Positive Exosite of Activated Protein C, The Journal of Biological Chemistry vol. 277, No. 32, 2002, pp. 28836-28840.
Gale et al., Nonenzymatic anticoagulant activity of the mutant serine protease Ser360Ala-activated protein C mediated by factor Va, Protein Science, 1997; 6:132-140.
Gale et al., The autolysis loop of activated protein C interacts with factor Va and differentiates between the Arg506 and Arg306 cleavage sites Blood, 2000, vol. 96, No. 2.
Gerlitz and Grinnell, Mutation of Protease Domain Residues Lys37-39 in Human Protein C Inhibits Activation by the Thrombomodulin-Thrombin Complex without Affecting Activation by Free Thrombin, The Journal of Biological Chemistry, 1996; vol. 271, No. 37, pp. 22285-22288.
Guo et al., Activated protein C prevents neuronal apoptosis via protease activated receptor 1 and 3, Neuron. 2004; 41:563-572.
He and Rezaie, Identification and characterization of the sodium-binding site of activated protein C. The Journal of Biological Chemistry, 1999; 274:4970-4976.
Hill and Castellino, The stimulation by monovalent cations of the amidase activity of bovine des-1-41 light chain activated protein C. The Journal of Biological Chemistry, 1986; 261:14991-14996.
Joyce et al., Gene expression profile of antithrombotic protein C defines new mechanisms modulating inflammation and apoptosis, The Journal of Biological Chemistry, 2001; 276:11199-11203.
Kalafatis et al., The mechanism of inactivation of human factor V and human factor Va by activated protein C. The Journal of Biological Chemistry, 1994; 269:31869-31880.
Kim et al., Vascular endothelial growth factor expression of intracellular adhesion molecule 1 (ICAM-1), vascular cell adhesion molecule 1 (VCAM-1), and E-selectin through nuclear factor kB activation in endothelial cells. The Journal of Biological Chemistry, 2001; 276:7614-7620.
Manithody et al., Exosite-dependent regulation of factor VIIIa by activated protein C. Blood. 2003; 101:4802-4807.

(Continued)

*Primary Examiner*—Sheridan Swope
(74) *Attorney, Agent, or Firm*—Randolph Bretton

(57) ABSTRACT

This invention relates to a novel form of protein C or activated protein C. More specifically, the invention is directed to a variant of protein C that is activated at a higher rate than wild-type or other variants and produces an activated protein C with reduced anticoagulant properties while retaining the protective anti-inflammatory and anti-apoptotic properties of wild-type activated protein C. This novel APC variant will be beneficial for treating inflammatory and apoptotic disorders with a reduced risk for bleeding.

15 Claims, 12 Drawing Sheets
(3 of 12 Drawing Sheet(s) Filed in Color)

OTHER PUBLICATIONS

Mosnier and Griffin, Inhibition of staurosporine-induced apoptosis of endothelial cells by activated protein C requires protease-activated receptor-1 and endothelial cell protein C receptor. Biochem J. 2003; 373:65-70.

Mosnier et al., Activated protein C variants with normal cytoprotective but reduced anticoagulant activity. Blood. 2004; 104:1740-1744.

Norstrom et al., Importance of protein S and phospholipid for activated protein C-mediated cleavage in factor Va., The Journal of Biological Chemistry, 2003; 278:24904-24911.

Oganesyan et al., The crystal structure of the endothelial protein C receptor and a bound phospholipid. The Journal of Biological Chemistry, 2002; 277:24851-24854.

Oren, Regulation of the p53 tumor suppressor protein. The Journal of Biological Chemistry, 1999; 274:36031-36034.

Perera et al., Modeling Zymogen Protein C Biophysical Journal vol. 79, 2000; 2925-2943.

Plutzky et al. Evolution and organization of the human protein C gene, PNAS 1986; vol. 83, pp. 546-550.

Rezaie and Esmon, Journal of Biological Chemistry, 1992 vol. 267, pp. 26104-26109, Yang et al., The Conformation of the Activation Peptide of Protein C Is Influenced by Ca2+ and Na+ Binding, The Journal of Biological Chemistry, 2004, vol. 279, No. 37, pp. 38519-38524.

Rezaie and Yang, Thrombomodulin allosterically modulates the activity of the anticoagulant thrombin, PNAS, 2003; vol. 100 No. 21,12051-12056.

Rezaie et al., Mutation of Glu 80 [to] Lys results in a protein C mutant that no longer requires Ca2+ for rapid activation by the thrombin-thrombomodulin complex. The Journal of Biological Chemistry, 1994; 269:3151-3154.

Riewald et al., Activation of Endothelial Cell Protease Activated Receptor 1, by the Protein C Pathway, Science. 2002, vol. 296, p. 1880.

Ruf et al., Specificity of coagulation factor signaling. J Thromb Haemost. 2003; 1:1495-1503.

Stearns-Kurosawa et al., The endothelial cell protein C receptor augments protein C activation by the thrombin-thrombomodulin complex. Proc Natl Acad Sci. (USA). 1996; 93:10212-10216.

Stenflo, Structure and function of protein C. Sem Thromb Hemost. 1984; 10:109-121.

Taylor et al., Protein C prevents the coagulopathic and lethal effects of *E coli* infusion in the baboon. J Clin Invest. 1987; 79:918-925.

Taylor et al., The endothelial cell protein C receptor aids in host defense against *Escherichia coli* sepsis. Blood. 2000; 95:1680-1686.

Walker and Fay, Regulation of blood coagulation by the protein C system. FASEB 1992; 6:2561-2567.

Yang et al., Activation of protein C by the thrombin-thrombomodulin complex: Cooperative roles of Arg-35 of thrombin and Arg-67 of protein C. Proc Natl Acad Sci. (USA) 2006; 103:879-884.

Yang et al., Identification of a Specific Exosite on Activated Protein C for Interaction with Protease Activated Receptor 1, The Journal of Biological Chemistry, 2007; vol. 282, No. 35, pp. 25493-25500.

Yang et al., The Conformation of the Activation Peptide of Protein C Is Influenced by Ca2+ and Na+ Binding, The Journal of Biological Chemistry, 2004, vol. 279, No. 37, pp. 38519-38524.

Yang et al., The functional significance of the autolysis loop in protein C and activated protein C. Thromb Haemostas. 2005; 94:60-68.

Zhang et al., Role of individual Gamma-Carboxyglutamic acid residues of activated human protein C in defining its in vitro anticoagulant activity. Blood. 1992; 80:942-952.

A

B

PROTEIN C VARIANT

RELATED APPLICATIONS

This patent application claims priority from U.S. provisional patent application Ser. No. 60/841,384, filed Aug. 31, 2006, which is incorporated herein by reference in its entirety.

GOVERNMENT SUPPORT CLAUSE

The work disclosed herein was supported by the National Heart, Lung, and Blood Institute of the National Institute of Health grant number HL 68571. The U.S. Government has certain rights in this invention.

BACKGROUND OF THE INVENTION

1. Field of the Invention

This invention relates generally to compositions and methods involved in the therapeutic use of protein C. Specifically, the invention is directed to a novel protein C that is activated by free thrombin at an increased rate, and upon activation, exhibits the protective anti-inflammatory and anti-apoptotic properties of wild-type activated protein C, but lacks the anti-coagulant properties responsible for excessive bleeding in some individuals. This novel protein C and its activated derivative may be useful for treating diseases which involve inflammation or apoptosis, such as severe sepsis.

2. Description of the Related Art

Activated protein C (APC), exhibits anti-inflammatory, cytoprotective, and potent anti-coagulant activity properties. In addition, recombinant activated protein C (APC) has been approved as a drug for treating severe sepsis, and has reduced mortality in these patients (See Bernard et al. (2001) N Eng J Med.; 344:699-709). Studies have also shown that APC may protect the endothelial cells of the brain from damage caused by ischemic stroke (Cheng et al. (2003) Nature Med.; 9:338-342).

There is growing evidence that the protective effects associated with APC when administered therapeutically are separate from its anti-coagulant effect, and that these protective effects are attributed to cell signaling by APC in the endothelium (Taylor et al. (1987) J Clin Invest. 1987; 79:918-925; Feistritzer et al. (2005) Blood; 105:3178-3184; Mosnier et al. (2003) Biochem J.; 373:65-70; Cheng et al. (2003) Nature Med.; 9:338-342; Guo et al. (2004) 41:563-572). An increased incidence of bleeding remains a major drawback of APC treatment (Bernard et al. (2001) N Eng J Med.; 344:699-709). This risk of bleeding prevents medical practitioners from fully utilizing APC therapy. Practitioners also require more treatment options, for example, a zymogen form of protein C that is more efficiently activated, particularly under inflammatory conditions. To our knowledge, these problems have not been solved. Protein C is activated inefficiently independent of the thrombin TM complex, and APC continues to include a high risk of bleeding. Therefore, there is a need for a protein C that is readily activated by free thrombin, and an APC with diminished anti-coagulant activity and normal cytoprotective properties.

SUMMARY OF THE INVENTION

The present invention relates to a variant of protein C and activated protein C whereby two cysteine residues are substituted for specific amino acids allowing the formation an intra-chain disulfide bond to cross-link the composition such that it possesses a new set of biological properties. The novel protein C is readily activated by free thrombin, and once activated exhibits cytoprotective properties without the increased risk of bleeding associated with the wild type activated protein C.

One embodiment the invention is drawn to a novel form of protein C, whereby one of amino acids 261-266 of SEQ ID NO:1 are cross-linked to one of amino acids 278-288 of SEQ ID NO:1. This cross-linking may be the result of a cysteine, substituted for an amino acid residue in each of these polypeptides sequences, whereby the substituted cysteines form a disulfide bond. This cross-linked protein C is distinguished from the wild type by exhibiting rapid activation by free thrombin.

Related to the novel form of protein C is an activated form of the variant whereby one of amino acids 261 to 266 of SEQ ID NO:1 are cross-linked to one of amino acids 278 to 288 of SEQ ID NO:1 and the activation peptide residues 200-211 of SEQ ID NO:1 is cleaved. This cross-linking may be the result of a cysteine, substituted for an amino acid residue in each of these polypeptides sequences, whereby the substituted cysteines form a disulfide bond. The activated form is distinguished from wild type by exhibiting cytoprotective properties and reduced anticoagulant activity.

In another embodiment, the invention is drawn to a method of manufacturing a cross-linked protein C, comprising the steps of (a) constructing an appropriate cDNA containing expression vector and (b) expressing the vector in a host cell.

Another embodiment relates to a cross-linked protein C in a pharmaceutically acceptable formulation for administration to a patient.

Another embodiment relates to a cross-linked activated protein C in a pharmaceutically acceptable formulation for administration to a patient.

Another embodiment relates to a method of treating an inflammatory disease such as sepsis, severe sepsis, or septic shock by administering cross-linked protein C or cross-linked activated protein C to the patient. Cross-linked protein C or cross-linked activated protein C may also be administered to treat a neurological disorder in a patient, of which ischemic stroke, Alzheimer's disease, Huntington disease, multiple sclerosis, ischemia, epilepsy, amyotrophic lateral sclerosis are examples.

REFERENCE TO COLOR FIGURES

The application file contains at least one figure executed in color. Copies of this patent application publication with color photographs will be provided by the Office upon request and payment of the necessary fee.

DETAILED DESCRIPTION OF THE INVENTION

Figure 1:
FIG. 1 illustrates the crystal structure of the catalytic domain of APC and positions of cysteine substitutions. The three-dimensional positions of Arg-67 (blue) and Asp-82 (red) on two anti-parallel beta structures of APC are shown. The catalytic residue Ser-195 (green) is also shown. The coordinates (Protein Data Bank entry 1AUT) were used to prepare the figure (Rezaie et al. (1994) J Biol Chem.; 269: 3151-3154).

I. Cross-linked Protein C and Cross-Linked Activated Protein C

The present invention relates to a method of forming cross-linked protein C. The invention also relates to the cross-linked protein C, which when activated forms a cross-linked activated protein C, that exhibits the same cytoprotection as wild type activated protein C except the newly formed cross-linked activated protein C does not have anticoagulant properties.

Cross-linked protein C was produced by the substitution of specific amino acids of the wild type human protein C polypeptide to alter functional properties such as activation by thrombin and anticoagulation, while leaving other properties such as cytoprotection intact. Therefore the following is a detailed description of the structure and function of the modified human protein C polypeptide that comprises cross-linked protein C and cross-linked activated protein C.

A. Protein C and Activated Protein C i Post-translational Modification

Wild type human protein C is the inactive zymogen form of a vitamin K-dependent plasma serine protease. Wild type protein C, in vivo, or as secreted by a eukaryotic cell in culture exists in the form of a disulfide-linked two chain molecule. It is transcribed as a single polypeptide (see SEQ ID NO:1), which then undergoes post-transitional modification. Modifications include removal of a signal peptide sequence (amino acids 1-42), and removal of a dipeptide sequence (amino acids 198-199), which produces two polypeptides referred to as the light (~25 kD) (amino acids 43-197) and heavy chains (~41 kD)(amino acids 200-461). Variations in molecular weight occur due to differences in glycosylation, which is also a post-translational modification. The light chain contains a region of gamma-carboxyglutamic acid, which is required for membrane binding and is dependent on $Ca^{2+}$. The heavy chain contains the serine protease domain, which also contains a $Ca^{2+}$ binding site described in detail below. The heavy chain also contains the activation peptide. Activation of protein C to activated protein C takes place in vivo by removable of this activation peptide (amino acids 200-211) by thrombin. A disulfide bond at cysteine 183 and cysteine 319 connects the heavy and light chains. (Plutzky et al., (1986) Proc. Natl. Acad. Sci. (USA) 83, 546-550)

ii Activation and Anticoagulation Activity

Protein C circulates as an inactive zymogen. Activation of protein C to activated protein C takes place by proteolytic removal of the activation peptide (amino acids 200-211, see SEQ ID NO:1) from the heavy chain. Protein C is activated on the surface of endothelial cells by a thrombin-thrombomodulin (thrombin-TM) complex, which is also accelerated by the endothelial protein C receptor (EPCR). This is believed to take place by co-locating protein C with the thrombin-TM complex on the endothelial cell surface (Stearns-Kurosawa et al. (1996) Proc Natl Acad Sci. (USA); 93:10212-10216). After activation, activated protein C down-regulates the clotting cascade via a feedback loop mechanism (Stenflo J. (1984) Thromb Hemost. 10:109-121; Esmon CT. (1993) Thromb. Haemost. 70:1-5). Once protein C is activated it may dissociate from EPCR, and form a complex with the vitamin K-dependent protein cofactor, protein S. This complex will shut down the generation of thrombin derived from the cofactor effect of factors Va (fVa) and VIIIa, which are known to be procoagulant cofactors of the prothrombinase and intrinsic Xase complexes, respectively (4-6).

iii Anti-inflammatory and Cytoprotective Properties

In addition to providing anti-coagulant activity, APC has anti-inflammatory and anti-apoptotic proprieties. When APC is associated with EPCR, it elicits protective signaling responses in endothelial cells (Taylor et al. (1987) J Clin Invest. 1987; 79:918-925; Taylor et al. (2000) Blood; 95:1680-1686; Joyce et al. (2001) J Biol Chem.; 276:11199-11203; Ruf et al. (2003) J Thromb Haemost. 1:1495-1503; Mosnier et al. (2004) Blood. 104:1740-1744; Finigan et al.

(2005) J Biol Chem.; 280:17286-17293). These protective signals may account for the beneficial effects associated with APC when used as an anti-inflammatory agent for treating severe sepsis patients (Bernard et al. (2001) N Eng J Med.; 344:699-709). The mechanisms of the anti-inflammatory and cytoprotective effects of APC are not well understood, however, it is believed that an APC/EPCR complex cleaves protease-activated receptor-1 (PAR-1) to initiate protective signaling events in endothelial cells (Ruf et al. (2003) J Thromb Haemost. 1:1495-1503; Mosnier et al. (2004) Blood. 104: 1740-1744). PAR-1 cleavage by APC may also be required for the inhibition of apoptosis in human brain endothelial cells induced by hypoxia (Cheng et al. (2003) Nature Med.; 9:338-342).

B. Cross-linked Protein C

The present invention alters the above-described protein C to produce a cross-linked protein C which is activated rapidly by free thrombin. Also, cross-linked protein C in its activated form demonstrates the cytoprotective properties of wild-type APC without the anti-coagulant properties. This is achieved by engineering a disulfide bond to form a cross-link between two anti-parallel β-sheets of the heavy chain polypeptide of human protein C. Specifically, amino acid residues at position 264 and also position 279 of wild type protein C (SEQ ID NO:1) are each substituted with cysteines, to produce a novel polypeptide (SEQ ID NO:2) (Bae et al. (2007) J Biol Chem.; 282: No. 12: 9251-9259). The presence of cysteines in these positions will allow the formation of an intra-chain disulfide bond post-translationally, thereby forming a cross-link between these two amino acids within the anti-parallel β-sheets of residues 261-266 and 278-288 of the protein C heavy chain (see FIG. 1). Similarly, the presence of cystines or another cross-linking agent, installed at one or more of these positions, within or near these anti-parallel β-sheets would produce a similar result. Between these anti-parallel β-sheets is the $Ca^{2+}$ binding 70-80 loop (CHT). While not agreeing to be bound by theory, one hypothesis is that the binding of $Ca^{2+}$ to the 70-80 loop of protein C is associated with a conformational change in the zymogen that is optimal for interaction with thrombin in the presence of TM but inhibitory for interaction in the absence of the cofactor (Yang et al. (2006) Proc Natl Acad Sci. (USA); 103:879-884). By cross-linking two anti-parallel β-sheets, the 70-80 calcium binding loop becomes stabilized and no longer binds $Ca^{2+}$. The engineered disulfide bond also stabilizes a $Na^+$ binding site in the high affinity state. These $Ca^{2+}$ and $Na^+$ binding sites modulate activation of protein C and may be necessary for the amidolytic activity and proteolytic activity demonstrated by APC, as described in detail below. The light chain of cross-linked protein C is not modified, and as in wild type, remains bound to the heavy chain by a single disulfide bond.

i Activation

Both wild type and cross-linked protein C may be activated by proteolytic removal of the activation peptide, amino acids 200-211 (SEQ ID NO:1), of the heavy chain. Wild type protein C binds to EPCR on the surface of endothelial cells where it is activated by the thrombin-TM complex. Endothelial cell surface receptors EPCR and TM improve the activation of wild type protein C by thrombin by three to four orders of magnitude and require $Ca^{2+}$ (Esmon CT. (1993) Thromb. Haemost. 70:1-5; Stearns-Kurosawa et al. (1996) Proc Natl Acad Sci. (USA); 93:10212-10216). The binding of $Ca^{2+}$ to a low affinity sites in the γ-carboxyglutamic acid (Gla) domain of protein C enables protein C to interact with EPCR on the surface of endothelial cells. This binding of $Ca^{2+}$, improves the Km of activation by the thrombin-TM complex (Stearns-Kurosawa et al. (1996) Proc Natl Acad Sci. (USA); 93:10212-10216; Oganesyan et al. (2002) J Biol Chem.; 277:24851-24854; Zhang et al. (1992) Blood; 80:942-952). The Gla domain is not altered in cross-linked protein C, and this binding may still occur. In addition, there exists another $Ca^{2+}$ binding site that is required for the thrombin-TM complex to activate wild type protein C at a physiologically relevant rate on the endothelial cell surface (Rezaie et al. (1994) J Biol Chem.; 269:3151-3154). The position of this high affinity $Ca^{2+}$ binding site has been localized to the 70-80 loop of protein C(CHT) (Bode et al. (1989) EMBO J.; 8:3467-3475). In addition to $Ca^{2+}$, $Na^+$ also modulates the catalytic function of APC (He et al. (1999) J Biol Chem.; 274:4970-4976; Hill et al. (1986) J Biol Chem.; 261:14991-14996). Recent studies conducted by the inventors have indicated that these $Ca^{2+}$, and $Na^+$ binding sites are energetically linked (He et al. (1999) J Biol Chem.; 274:4970-4976). The binding of $Ca^{2+}$ as well $Na^+$ produces distinct functional changes in the conformation of the activation peptide (Likui et al. (2004) J Biol Chem, Vol. 279, No. 37, Issue of September 10, pp. 38519-38524). While not agreeing to be bound by theory, the engineered disulfide bond may prevent or alter changes normally caused by binding of these ions. This may account for the enhanced activation of cross-linked protein C by free thrombin, independent of TM in the presence of $Ca^{2+}$ as demonstrated in the examples.

ii Anticoagulant Activity and Anti-Inflammatory and Cytoprotective Properties

The mechanism through which wild type protein C, once activated, functions in the anti-coagulant pathway has been extensively studied and is well understood (Walker et al. (1992) FASEB J; 6:2561-2567). After activation, APC may dissociate, from EPCR and bind to protein S, where it functions as an anticoagulant by degrading factors Va and VIIIa. Specific recognition of procoagulant factors Va and VIIIa, is determined by the basic residues of an APC exosite (Friedrich et al. (2001) J Biol Chem.; 276:23105-23108; Manithody et al. (2003) 101:4802-4807; Gale et al. (2002) J Biol Chem.; 277:28836-28840). These basic residues are clustered on three exposed surface loops referred to as 37-39 loop, 60-68 loop and 70-80 loop (CHT) (Bode et al. (1989) EMBO J.; 8:3467-3475). These basic residues constitute a binding site for TM in the thrombin-TM complex. With the exception of the 60 loop, they are also involved in recognition and subsequent degradation of factors Va and VIIIa by APC in the anti-coagulant pathway (Friedrich et al. (2001) J Biol Chem.; 276:23105-23108; Manithody et al. (2003) Blood; 101:4802-4807; Gale et al. (2002) J Biol Chem.; 277:28836-28840). Again, while not agreeing to be bound by theory, the anti-coagulant function of APC may require the cofactor functions of the metal ions $Ca^{2+}$ and $Na^+$ both of which allosterically modulate the structure and catalytic function of APC (He et al. (1999) J Biol Chem.; 274:4970-4976). Such a coordinated metal ion modulation of the APC structure and function has been disrupted in cross-linked APC since the engineered disulfide bond may abolish the requirement for $Ca^{2+}$ and, also may stabilize the $Na^+$ binding site of in the high affinity state. These structural changes may be important for the anti-coagulant function but not for the protective signaling effects of APC. Therefore, the engineered disulfide bond has provided changes in structure, which have in turn cause changes in biological function. These changes include the reduction or elimination of anti-coagulant activity normally associated with wild-type activated protein C, while preserving normal cytoprotective properties. This elimination of anti-coagulant properties is further described and demonstrated in the examples.

As described above (IAiii), wild type activated protein C also possesses cytoprotective properties. These activities are mediated through endothelial cell binding which takes place via the Gla domain (amino acids 43-88 of SEQ ID NO:1). The Gla domain is not altered in cross-linked protein C, and biological activity of the Gla domain remains unchanged. Therefore, similar to wild type, endothelial cell binding via the Gla domain still occurs. Cross-linked APC may participate in anti-inflammatory and anti-apoptotic activities in the same manner as wild-type APC. These properties are further described and demonstrated in the examples.

Therefore, by specifically engineering specific regions of the protein C polypeptide, while leaving other regions intact, the anti-coagulant activity of cross-linked APC is essentially abolished, while it's anti-inflammatory and cytoprotective signaling properties remain intact.

The properties described herein for cross-linked protein C or cross-linked activated protein C may allow its use in a wider therapeutic range. For example, it may be possible for medical practitioners to administer greater amounts of cross-linked protein C, as the zymogen form will circulate until activated on demand by endogenous thrombin. Alternatively, or in addition to, medical practitioners may be able to administer higher levels of cross-linked APC as patients may better tolerate cross-linked APC with a reduced risk of bleeding. Also, enhanced immunogenicity is often a problem with altered proteins, including variants of APC that are being developed as therapeutic drugs. The instant invention reduces the likelihood an immunogenic problem, since no surface residues have been altered.

Cross-linked protein C, is activated rapidly by free thrombin and once activated, provides anti-inflammatory and anti-apoptotic protection without anticoagulation effects. This distinct set of biological activities is not known in other variants of protein C. This novel cross-linked protein C and its activated derivative may be safer than wild-type or other variants of APC for treating patients with an inflammatory or apoptotic disorder including but not limited to sepsis, severe sepsis, or septic shock. Cross-linked PC and cross-linked APC may also be useful for treating patients with disorders including inflammatory bowel disease, vasculitis, renal ischemia, and pancreatitis. Cross-linked APC may also be useful for treating disorders including neurological disorders such as ischemic stroke, Alzheimer's disease, Huntington disease, multiple sclerosis, ischemia, epilepsy, amyotrophic and lateral sclerosis.

Describe herein are various properties of cross-linked protein C and cross-linked APC including activation, anti-coagulant, anti-inflammatory, anti-apoptotic and protective endothelial barrier permeability. The methods disclosed to illustrate these properties are intended to be exemplary only and not intended to exclusively define the instance invention. Numerous methods of measuring anti-coagulant, anti-inflammatory, anti-apoptotic and endothelial barrier permeability are well known in the art which may be also expected to demonstrate the properties of cross-linked APC as disclosed herein.

C. Method of Making Cross-linked APC

The method for making cross-linking protein C involves methodology that are generally well known and described in detail in numerous laboratory protocols, one of which is Molecular Cloning 3rd edition, (2001) J. F. Sambrook and D. W. Russell, ed., Cold Spring Harbor University Press. Many modifications and variations of the present illustrative DNA sequences and plasmids are possible. For example, the degeneracy of the genetic code allows for the substitution of nucleotides throughout polypeptide coding regions, as well as in the translational stop signal, without alteration of the encoded polypeptide coding sequence. Such substitutable sequences can be deduced from the known amino acid or DNA sequence of human protein C and can be constructed by following conventional synthetic or site-directed mutagenesis procedures. Synthetic methods can be carried out in substantial accordance with the procedures of Itakura et. al., (1977) Science 198:1056 and Crea et. al. (1978) Proc. Natl. Acad. Sci, USA 75:5765. Therefore, the present invention is in no way limited to the DNA sequences and plasmids specifically exemplified.

A polynucleotide encoding human protein C polypeptide (SEQ ID NO:1) or variants thereof, may be engineered whereby the codons representing one or more of amino acids 261 to 266 and one or more of amino acids 278 to 288 are replaced with codons for cysteine. By way of non-limiting example, and as described below in the examples, nucleotide sequences complementary for a polynucleotide encoding these amino acid sequences may be constructed whereby codons representing amino acid 264 and amino acid 279 are substituted by a cysteine. One of ordinary skill in the art will understand that other codons representing other or additional amino acids within these complementary nucleotide sequences may be replaced with codons for cysteine to provide alternative or additional cysteine substitutions in a similar manner.

Examples of protein C derivatives are described by Gerlitz, et al., U.S. Pat. No. 5,453,373, and Foster, et al., U.S. Pat. No. 5,516,650, the entire teachings of which are hereby included by reference. By way of example primers described in the examples The polynucleotide may then be amplified using standard PCR mutagenesis methods as previously described (Rezaie et al. (1992) Journal of Biological Chemistry, vol. 267, pp. 26104-26109) and herein incorporated by reference. The resulting mutant protein C cDNA may be sub-cloned and inserted into a suitable expressions vector using a number of commercially available restrictions enzymes and expressed in a wide variety of eukaryotic, especially mammalian, host cells. The polynucleotide may be operable linked to a number of suitable control elements to provide an expressible nucleic acid molecule by using standard cloning or molecular biology techniques. See, e.g., Edge (1981) Nature 292:756; Nambair et al. (1984) Science 223:1299; and Jay et al. (1984) J. Biol. Chem. 259:6311. Examples of expression vectors that may be effective for the expression of cross-linked protein C include, but are not limited to, the PCDNA 3.1, EPITAG, PRCCMV2, PREP, PVAX, PCR2-TOPOTA vectors (Invitrogen, Carlsbad Calif.), PCMV-SCRIPT, PCMV-TAG, PEGSHIPERV (Stratagene, La Jolla Calif.), and PTET-OFF, PTET-ON, PTRE2, PTRE2-LUC, PTK-HYG (Clontech, Palo Alto Calif.). Cross-linked protein C may be expressed using (i) a constitutively active promoter, (e.g., from cytomegalovirus (CMV), Rous sarcoma virus (RSV), SV40 virus, thymidine kinase (TK), or P.beta.actin genes), (ii) an inducible promoter (e.g., the tetracycline-regulated promoter (Gossen et al. (1992) Proc. Natl. Acad. Sci. USA 89:5547-5551; Gossen, M. et al. (1995) Science 268:1766-1769; Rossi et al. (1998) Curr. Opin. Biotechnol. 9:451-456), commercially available in the T-REX plasmid (Invitrogen).

Once constructed, the expression vector encoding cross-linked protein C may be transfected into host cells using standard gene delivery protocols. Methods for gene delivery are known in the art, and include but are not limited to methods based on naked nucleic acids, calcium phosphate, electroporation, microinjection liposomes, cells, retrovirus including lentiviruses, adenovirus and parvoviruses including adeno-associated virus herpes simplex virus. See, e.g., U.S. Pat. Nos. 7,173,116 6,936,272, 6,818,209, and 7,232, 899, which are hereby incorporated by reference. Other gene delivery mechanisms include liposome-derived systems, artificial viral envelopes, and other systems known in the art (See, e.g., Rossi, J. J. (1995) Br. Med. Bull. 51(1):217-225; Boado, R. J. et al. (1998) J. Pharm. Sci. 87(Mosnier et al. (2004) Blood. 104:1740-1744):1308-1315; and Morris, M. C. et al. (1997) Nucleic Acids Res. 25(14):2730-2736)

Techniques for maintaining cells in culture to allow the expression of recombinant polypeptides are well known. By way of example the polynucleotide described above may be expressed in human embryonic kidney cells (HEK-293) using the RSV-PL4 expression system purification vector system as described (Yang et al. (2006) Proc Natl Acad Sci. (USA); 103:879-884) and Yan, U.S. Pat. No. 4,981,952, both of which are hereby incorporated by reference.

Cross-linked protein C may be harvested from the culture media and purified through any combination of protein purification techniques known in the art including various immuno-affinity techniques. An antibody directed to almost any epitope on cross-linked protein C may be immobilized to a support structure. A physiological solution containing the molecule to be purified is exposed to the antibody whereby the target molecule is bound by the antibody. Methods of releasing polypeptides from antibodies are also well known and may include changes in pH, and elution with various salts, metal ions, EDTA, EGTA, or detergents.

Cross-linked activated protein C may be produced from cross-linked protein C by incubation with a proteolytic enzyme such as thrombin in a physiological solution. By way of example a solution containing physiological salts and cross-linked protein C may be passed over a column comprising thrombin immobilized to Sepharose. Alternatively, cross-linked activated protein C may be produced directly by expression of a polynucleotide engineered to transcribe a cross-linked activated protein C.

Several other cross-linking methodologies may also allow for the formation of covalent bonds suitable for making cross-linked protein C or cross-linked activated protein C. Polar or non-polar functional groups of amino acids may show an affinity for one another, which may be exploited and stabilized. By way of non-limiting example, tyrosine substitution with di-tyrosine cross-linking is described in U.S. Pat. No. 7,037,894, and is herein incorporated by reference in its entirety. Similar to the substitution of cysteine, one or more of amino acids 261 to 266 of SEQ ID NO:1 and one or more of amino acids 278 to 288 of SEQ ID NO:1 may be substituted with tyrosine, which may later cross-linked through oxidation. Once two tyrosine aromatic functional groups are in close proximity to one another, cross-links may occur naturally, for example as catalyzed in vivo by cytochrome c, peroxidase or by metallo-ion complexes. Alternatively dityrosyl cross-links may be formed as described in U.S. Pat. No. 7,037,894.

Another method of cross-linking protein C or activated protein C may be to utilize immuno-cross-linking-techniques. By way of non-limiting example, a monoclonal antibody may be raised against an epitope that comprises the anti-parallel β-sheets in the stabilized configuration. Fab or Fv fragments of such an antibody may be produced and incubated with protein C or activated protein C to stabilize the polypeptide in the cross-linked configuration describe above. Techniques of making monoclonal antibodies and their fragments are well known in the art.

Alternatively, chemical cross-linking agents may be utilized. Many chemical cross-linking agents are commercially available, which specifically react with amino acid functional groups (Pierce Rockford, Ill.). Also, methods of treating the proteins with formamide, glutaraldehyde or UV-radiation are well known and may also be suitable for producing cross-linked protein C or cross-linked activated protein C. These methodologies would allow cross-linking to be performed on purified wild type or variants of protein C or activated protein C. In the practice of these methods, it is routine for the artisan to vary time and concentration of protein and cross-linking agent to optimize conditions. However, as these cross-linking methods are non-directed, a number of non-functional molecules may be produce. Therefore the specific activity of the cross-linked preparation may need to be determined after cross-linking, and the treatment regime or dosage adjusted appropriately. Specific activity may be determined, by way of example, using any of the in vitro assays described in the examples. It may be beneficial to mask function regions of protein C such as the Gla region and the activation peptide while using non-directed chemical cross-linkers to preserve activity.

II. Formulations and Administration of Cross-linked APC

A. Pharmaceutical Dosage Form

A pharmaceutically acceptable formulation of cross-linked PC, or cross-linked APC may be an injectable physiological solution. Cross-linked PC, and cross-linked APC are hydrophilic polypeptides and may be administered intravenously in a sterile aqueous solution, preferable a physiological solution. A physiological solution may be comprised of isotonic balanced salts with a pH of about 7.0 to about 7.5. A preferred physiological solution may comprise isotonic saline and a pH of 7.5. A single-time (bolus) injection is a possibility, as is continuous infusion.

The aqueous solution may further contain various salts or buffers that are well known in the art. Injectable preparations, for example, sterile injectable aqueous or oleaginous suspensions, may be formulated according to the known art using suitable dispersing or wetting agents and suspending agents. The sterile injectable preparation may also be a sterile injectable solution or suspension in a nontoxic parenterally acceptable diluent or solvent. Among the acceptable vehicles and solvents that may be employed are, Ringer's solution, or isotonic sodium chloride solution.

It is preferable to maintain the pH in a physiological range, from about 6.0 to about 6.5, or about 6.5 to about 7.0, or about 7.0 to about 7.5, or about 7.5, to about 8.0, preferably about 7.0 to about 7.5. To maintain effective pH control, the cross-linked protein C or cross-linked activated protein C solution should contain a pharmaceutically acceptable buffer.

Similarly, it is preferable to maintain the ionic strength in a physiological range. The ionic strength is generally determined by the salt concentration of the solution. Pharmaceutically acceptable salts typically used to generate ionic strength include but are not limited to potassium chloride (KCl) and sodium chloride (NaCl). The preferred salt is maintained is a physiological range, by way of example sodium chloride may be used at a concentration of 0.9 percent by weight.

Formulations developed for protein C or activated protein C are also known in the art and may also be used for cross-linked protein C or cross-linked activated protein C, including those described in U.S. Pat. Nos. 6,630,137, 6,159,468, and 6,395,270 which are hereby incorporated by reference.

Cross-linked protein C or cross-linked activated protein C may be formulated to prepare a pharmaceutical composition comprising as the active agent, cross-linked protein C or cross-linked activated protein C, and a pharmaceutically acceptable solid or carrier. For example, a desired formulation would be one comprising a bulking agent such as sucrose, a salt such as sodium chloride, a buffer such as sodium citrate and cross-linked protein C or cross-linked activated protein C. Formulations may be lyophilized for storage, and hydrated before use. Examples of stable lyophilized formulations include 5.0 mg/ml activated protein C, 30 mg/ml sucrose, 38 mg/ml NaCl and 7.56 mg/vial citrate, pH 6.0; and, 20 mg/vial activated protein C, 120 mg/ml sucrose, 152 mg/vial NaCl, 30.2 mg/vial citrate, pH 6.0.

Alternatively, cross-linked PC, or cross-linked APC formulated into pharmaceutical compositions and administered by a number of different means that will deliver a therapeutically effective dose. Such compositions may be administered, by way of example parenterally, including subcutaneously, intravenously, intramuscularly, or by intrathecal injection or infusion techniques. Additionally, a compound may be administered topically, including intradermally or transdermally. Also included is transmucosal administration including intranasal absorption through the mucous membrane by inhalation spray or insufflation. Formulation of drugs is discussed in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980).

B. Administration of Therapeutic Amounts

Cross-linked protein C and cross-linked activated protein C retain the anti-inflammatory and anti-apoptotic properties of wild-type APC. These beneficial properties are responsible for the therapeutic effects observed when APC is used to treat inflammatory disorders in patients. Therefore, a disease or disorder that may be treated with protein C or activated protein C, may also be treated with cross-linked protein C or cross-linked activated protein C. In addition, cross-linked PC and cross-linked APC retain these cytoprotective properties at approximately the same or only slightly reduced levels compared to wild type molecules. Therefore, cross-linked protein C and cross-linked activated protein C may be administered in approximately the same treatment regiments as used for PC, APC, or variants thereof. Generally, a greater amount of the zymogen (2-10 fold) may be administered for the equivalent effective amount of the activated molecule. Furthermore, with a reduced risk of bleeding, cross-linked PC and cross-linked APC may be administered at higher levels than other forms of protein C or APC.

The following are examples of treatment regimes which may be used to administer cross-linked protein C or cross-linked activated protein C to treat a condition of inflammation or apoptosis including but not limited to sepsis, severe sepsis, septic shock, inflammatory bowel disease, vasculitis, renal ischemia, and pancreatitis ischemic stroke, Alzheimer's disease, Huntington disease, multiple sclerosis, ischemia, epilepsy, amyotrophic and lateral sclerosis. Treatment regimes for activated protein C are described in U.S. Pat. Nos. 6,037,322, 6,156,734, and 7,204,981 which are hereby incorporated by reference. For the reasons described in this section, cross-linked protein C or cross-linked activated protein may be administered in a similar manner.

Cross-linked protein C or cross-linked activated protein C may be administered as a continuous infusion for about 1 to about 240 hours, about 1 to about 196 hours, or about 1 to about 144 hours, or about 1 to about 96 hours, or about 1 to about 48 hours, or about 1 to about 24 hours, or about 1 to about 12 hours, or less. Preferably, cross-linked protein C or cross-linked activated protein C will be administered as a continuous infusion for about 1 to about 96 hours.

The amount of cross-linked activated protein C administered by continuous infusion may be from about 0.01 µg/kg/hr to about 50 µg/kg/hr, about 0.1 µg/kg/hr to about 40 µg/kg/hr, or about 1 µg/kg/hr to about 30 µg/kg/hr. Preferable amounts of cross-linked activated protein C administered may be about 24 µg/kg/hr.

The plasma ranges obtained from the amount of cross-linked activated protein C administered may be about 0.02 ng/ml to about 200 ng/ml, about 0.2 ng/ml to about 100 ng/ml, about 2 ng/ml to about 60 ng/ml. Preferred plasma ranges may be about 40 ng/ml to about 50 ng/ml.

Increased amounts of cross-linked protein C may be administered for the equivalent effective of cross-linked activated protein C. Therefore, the amount of cross-linked protein C administered by continuous infusion may be from about 0.01 µg/kg/hr to about 500 µg/kg/hr, about 0.1 µg/kg/hr to about 400 µg/kg/hr, or about 1 µg/kg/hr to about 300 µg/kg/hr. Preferable amounts of cross-linked protein C administered may be about 240 µg/kg/hr.

The plasma ranges obtained from the amount of cross-linked protein C administered may be about 0.02 ng/ml to about 2000 ng/ml, about 0.2 ng/ml to about 1000 ng/ml, about 2 ng/ml to about 600 ng/ml. Preferred plasma ranges may be about 40 ng/ml to about 500 ng/ml.

Plasma levels of cross-linked protein C or cross-linked activated protein may be determined as described in U.S. Pat. No. 6,037,322, hereby incorporated by reference in its entirety, or through standard immunochemical means known in the art including Enzyme-Linked ImmunoSorbent Assay (ELISA). Cross-linked activated protein C may also be measured by determining amidolytic activity as described in the examples. By way of example, plasma levels may be calculated from pretreatment and post treatment measurements.

In another alternative, cross-linked protein C or cross-linked activated protein C will be administered by injecting a portion (about ⅓ to about ½) of the appropriate dose per hour as a bolus injection over a time from about 5 minutes to about 120 minutes, followed by continuous infusion of the appropriate dose for up to about 240 hours.

In another alternative, cross-linked protein C or cross-linked activated protein may be administered parenterally to ensure delivery into the bloodstream in an effective form by injecting a dose of about 0.01 mg/kg/day to about 10.0 mg/kg/day, B.I.D. (2 times a day), for one to about ten days. Preferably, the protein C will be administered B.I.D. for about three days.

In yet another alternative cross-linked protein C or cross-linked activated protein C may be administered subcutaneously at a dose of about 0.01 mg/kg/day to about 10.0 mg/kg/day, to ensure a slower release into the bloodstream. Formulation for subcutaneous preparations will be done using known methods to prepare such pharmaceutical compositions.

The above treatment regiments and dosages of cross-linked protein C or cross-linked activated protein C are non-limiting. A skilled artisan may determine the dosages based on a particular patient and a particular disease. It is anticipated that treatment regimes of protein C or activated protein C may be used as a guide, including treatment regimes know or indicated for Xigris® (i.e. 24 mcg/kg/hr IV for 96 hrs), a recombinant activated protein C. However, it may be possible to administer increased amounts of cross-linked protein C or cross-linked activated protein C due to reduced anti-coagulant activity and decreased risk of bleeding.

III. Therapeutic Applications of APC

Disorders Caused by Inflammation and Apoptosis

A. Sepsis

Activated protein C has been used for treatment of severe sepsis, including as described in U.S. Pat. No. 6,489,296, herein incorporated by reference in its entirety. Sepsis is a systemic reaction characterized by arterial hypotension, metabolic acidosis, decreased systemic vascular resistance, tachypnea and organ dysfunction. Sepsis can result from septicemia, including bacteremia, as well as toxemia, including endotoxemia. The term "bacteremia" includes occult bacteremia observed in young febrile children with no apparent foci of infection. The term "sepsis" also encompasses fungemia, viremia, and parasitemia. Thus, septicemia and septic shock (acute circulatory failure resulting from septicemia often associated with multiple organ failure and a high mortality rate) may be caused by a number of organisms. The criteria for diagnosing an adult with sepsis do not apply to infants under one month of age. In infants, only the presence of infection plus a "constellation" of signs and symptoms consistent with the systemic response to infection are required for diagnosis (Oski's Pediatrics, 2006).

Sepsis is considered to be present if infection is suspected or demonstrated and two or more of the following systemic inflammatory response syndrome (SIRS) criteria are met: heart rate is greater than 90 beats per minute; body temperature is less than 36° C. or greater than 38° C.; respiratory rate is greater than 20 breaths per minute; or, on blood gas, a $P_aCO_2$ less than 32 mm Hg; white blood cell count is less than 4000 cells/mm$^3$ or greater than 12000 cells/mm$^3$, or greater than 10% band forms as an indication of immature white blood cells. Patients are defined as having "severe sepsis" if they have sepsis plus signs of systemic hypoperfusion, either end organ dysfunction or a serum lactate greater then 4 mmol/dL.

Patients are defined as having septic shock if they have sepsis plus hypotension after an appropriate fluid bolus (typically 20 ml/kg of crystalloid). To diagnose "septic shock", sepsis must be present as defined above, and the following two criteria must be met: evidence of infection, through a positive blood culture; and refractive hypotension which is defined as hypotension despite adequate fluid resuscitation. In adults it may be defined as a systolic blood pressure less than 90 mmHg, or a MAP less than 60 mmHg, or a reduction of 40 mmHg in the systolic blood pressure from baseline. In children it is BP less than 2 SD of the normal blood pressure.

Successful treatment of sepsis, sever sepsis, or septic shock may be determined by a return toward normalcy of any of the symptoms used above to describe sepsis, sever sepsis, or septic shock and a decrease in mortality. In addition to the treatment regiums described above (see section IIIB), treatment of sepsis, sever sepsis or septic shock may be treated as described in U.S. Pat. No. 6,489,296 whereby cross-linked APC is substituted for wild type APC. For the reasons described in section IIB, cross-linked protein C or cross-linked activated protein may be administered in a similar manner. Cross-linked protein C and cross-linked activated protein C may be administered in addition to or in combination with other known treatments, for example appropriate hydration and/or antimicrobials, such as antibiotics, antifungal, antiviral and antiparasitic agents.

B. Ischemic Stroke

Successful treatment of ischemic stroke, vascular occlusion may be determined by increase in reperfusion, or return of neurological function, including a decrease in disabilities or mortality. In addition to the methods of administration of cross-linked protein C or cross-linked activated protein C generally described above (see section IIIB), treatment of ischemic stroke, vascular occlusion, and thromboembolic disorders may also be treated, by way of non-limiting example as in Example 7 (2.0 mg/kg slow iv bolus for 15 minutes), or, as described in U.S. Pat. Nos. 6,037,322 and 6,268,337 and (i.e. 0.05 mg/kg/hr for a 96 hr), 5,084,274 (i.e. 0.2 mg/kg/hr to 1.1 mg/kg/hr activated protein C alone or in combination with a thrombolytic agents) and European Patent Specification EP 0 318 201 B1. Cross-linked protein C and cross-linked activated protein C may be administered in addition to or in combination with other known treatments, for example appropriate hydration and antiplatelet therapy or tPA.

Other diseases or disorders which may be treated by cross-linked protein C or cross-linked activated protein C include but are not limited to: inflammatory bowel disease, vasculitis, renal ischemia, and pancreatitis (i.e. 1 µg/kg/hr to about 50 µg/kg/hr activated protein C by continuous infusion for about 1 to about 240 hours), as described in U.S. Pat. No. 7,204,981 and herein incorporated by reference in its entirety. Also included are multiple sclerosis, Hashimoto's thyroiditis, Graves Disease, chronic hepatitis, systemic lupus erythematosus, Alzheimer's disease or Parkinson's disease, (i.e. subcutaneously at a dose of 0.5 mg/day), as also described in U.S. Pat. No. 7,204,981. Also included are neuropathological disorders including but not limited to stroke, Alzheimer's disease, Huntington disease, multiple sclerosis (MS), ischemia, epilepsy, amyotrophic and lateral sclerosis as described in U.S. Pat. No. 7,074,402, and hereby incorporated by reference. Cross-linked protein C and cross-linked activated protein C may be administered in addition to or in combination with other known treatments.

DEFINITIONS

The term "protein C" or "PC" refers to the inactive or zymogen form of activated protein C whether isolated from nature or produced through recombinant DNA methodology and includes all precursors, derivatives, variants, truncated variants, mutants, or analogs of PC which possess at least one functional property associated with wild type protein C, or upon activation with wild type activated protein C. Also included in this definition is the full length unmodified polypeptide of SEQ ID NO:1, and activated protein C. Non-limiting examples of protein C derivatives are also described by Gerlitz et al., U.S. Pat. No. 5,453,373, and Foster et al., U.S. Pat. No. 5,516,650, the entire teachings of which are hereby included by reference.

The term "activated protein C" or "APC" refers generally to the activated form of protein C as defined in this section including wild-type activated protein C whether isolated from nature or produced through recombinant DNA methodology.

The term "cross-linked" refers to the formation of a covalent chemical linkage between two amino acid residues, or two polypeptide chains. Where those residues are cysteine cross-linked refers to the formation of a disulfide bond.

The term "cross-linked protein C" or "cross-linked PC" refers to protein C that is the zymogen or precursor form of activated protein C wherein one or more of amino acid residues 261 to 266 of SEQ ID NO:1 (64-69 chymotrypsin numbering (CHT)) have been cross-linked to one or more of amino acid residues 278-288 of SEQ ID NO:1 (81-91 CHT) to stabilize or modify biological properties. Cross-linked protein C as used herein includes all precursors, derivatives, variants, truncated variants, mutants, or analogs of PC, which contain the above, mentioned cross-linked amino acids.

The term "cross-linked activated protein C" or "cross-linked APC" refers to the activated form of cross-linked protein C as defined in this section.

The term "Cys-67-82 protein C" or "Cys-67-82 PC" refers to one embodiment of the instance invention whereby the inventors have replaced the amino acid at position 67 (CHT) (264 of SEQ ID NO:1) with cysteine, and amino acid at position 82 (CHT) (279 of SEQ ID NO:1) with cysteine, of human protein C to allow formation of a disulfide bond, thereby cross-linking two anti-parallel β-sheet polypeptide structures of the composition.

The term "Cys-67-82 activated protein C", or "Cys-67-82 APC" or "mutant APC" refers to the activated form of Cys-67-82 protein C, or Cys-67-82 PC.

The term "activation" as used herein refers to the enzymatic cleavage of the protein C to release polypeptide residues 200-211 of SEQ ID NO:1.

Through out this disclosure the inventors refer to amino acid sequences and specific amino acids using the "chymotrypsin numbering system" or "CHT." This system was set forth by Bode et al., (Bode et al. (1989) EMBO J.; 8:3467-3475). Included in this disclosure is a human protein C amino acid sequence (Accession number NP_000303) (SEQ ID NO:1). By way of reference and example, Cys-67-82 corresponds to the substitution of cysteine for amino acids 264 and 279 of SEQ ID NO:1 respectively, whereas the $Ca^{2+}$ binding 70-80 loop corresponds to amino acids 267-277 of SEQ ID NO:1.

The term "cytoprotective" refers to protection of cells in a patient from damage caused by conditions including but not limited to inflammation and apoptosis.

The term "anti-apoptotic" refers to protective effect whereby APC prevents or reduces the number of cells that will enter apoptosis or programmed cell death.

The term "in combination with" refers to the administration of a compound with cross-linked protein C or cross-linked activated protein C, either simultaneously, sequentially, or a combination thereof.

Sequence identity or percent identity is intended to mean the percentage of same residues between two sequences. In sequence comparisons, the two sequences being compared are aligned using the Clustal method (Higgins et al, Cabios 8:189-191, 1992) of multiple sequence alignment in the Lasergene biocomputing software (DNASTAR, INC, Madison, Wis.). In this method, multiple alignments are carried out in a progressive manner, in which larger and larger alignment groups are assembled using similarity scores calculated from a series of pairwise alignments. Optimal sequence alignments are obtained by finding the maximum alignment score, which is the average of all scores between the separate residues in the alignment, determined from a residue weight table representing the probability of a given amino acid change occurring in two related proteins over a given evolutionary interval. Penalties for opening and lengthening gaps in the alignment contribute to the score. The default parameters used with this program are as follows: gap penalty for multiple alignment=10; gap length penalty for multiple alignment=10; k-tuple value in pairwise alignment=1; gap penalty in pairwise alignment=3; window value in pairwise alignment=5; diagonals saved in pairwise alignment=5. The residue weight table used for the alignment program is PAM250 (Dayhoff et al., in Atlas of Protein Sequence and Structure, Dayhoff, Ed., NBRF, Washington, Vol. 5, suppl. 3, p. 345, 1978).

Variations in the amino acid sequence will likely be comprised of conservative amino acid substitutions, or substitutions of amino acids outside of functions regions such as the Gla region, the catalytic region, or the activation peptide as described herein.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples.

EXAMPLES

A novel protein C was created with a unique set of biological properties. As will be shown, the unique properties include increased activation by free thrombin, with the resulting activated form demonstrating greatly reduced anti-coagulation activity, with the anti-inflammatory, anti-apoptotic activity of the wild type molecules. The novel protein C includes a disulfide bond that has been engineered to be located between two anti-parallel β-structures of protein C, the bond forms a cross-link and stabilizes the 70-80 $Ca^{2+}$ binding loop.

Arginine at position 67 (Arg-67) and Aspartic acid at position 82 (Asp-82) was replaced with cysteine to create a disulfide bond between the respective polypeptide structures. As will be shown the cross-linked protein C can be activated by free thrombin 60-80 times more efficiently than wild-type protein C. It was further observed that cross-linked activated protein C (Cys-67-82 APC) retained its anti-inflammatory and anti-apoptotic protective properties but demonstrated a loss of anti-coagulant activity shown in both in vitro and in vivo assays. It was observed that the protective signaling effects of the cross-linked APC were slightly reduced (½) as determined in vitro by apoptosis, permeability, and leukocyte adhesion and migration assays in EA.hy926 endothelial cells.

The engineered disulfide bond appears to stabilize the APC mutant in a conformation that is incapable of cleaving procoagulant cofactors, but capable of interacting with the target cytoprotective endothelial cell signaling molecules. Thus, this cross-linked APC may be a safer drug for treating severe sepsis and other inflammatory or apoptotic disorders in patients who are at higher risk of bleeding due to the anti-coagulant function of APC.

Reagents

Staurosporine was purchased from Calbiochem (San Diego, Calif.). The following antibodies were used for Western blots: polyclonal human AIF (1:1000), Bax (1:100, Chemicon, Temecula, Calif.), human p53 (1:1000, Cell Signaling, Beverly, Mass.), human Bcl-2 (1:100, Santa Cruz Biologics, Santa Cruz, Calif.), and actin (1:5000, Sigma, St Louis, Mo.). Antibodies blocking activation of PAR-1 (H-111, Santa Cruz Biologics, Santa Cruz, Calif.) or non-blocking (S-19, Santa Cruz Biologics, Santa Cruz, Calif.) were used at 25 μg/ml. Function-blocking EPCR antibody (clone RCR-252; Cell Sciences, Canton, Mass.) was also used at 25 μg/ml. Tumor necrosis factor-α (TNF-α) was purchased from R&D System (Minneapolis, Minn.). Human plasma fVa, factor Xa and antithrombin were purchased from Haematologic Technologies Inc. (Essex Junction, Vt.), and Spectrozyme PCa was purchased from American Diagnostica (Greenwich, Conn.).

Construction and Expression of Recombinant Proteins The amino acid sequence for Protein C has previously been described (Beckmann et al. (1985) Nucleic Acids Res. vol. 13 pp. 5233-5247; Plutzky et al. (1986) PNAS Vol. 83, pp 546-550), and is represented by SEQ ID NO:1 (Accession number NP_000303, NBCI). Elements of the inventors' methodology not described herein are generally well known and detailed in numerous laboratory protocols, including Molecular Cloning 2nd edition, (1989) Sambrook, J., Fritsch, E. F., and Maniatis, J., Cold Spring Harbor, and Current Protocols in Molecular Biology, volumes 1-3, John Wiley & Sons, Inc. herein incorporated by reference.

Wild-type protein C and the cross-linked protein C, (Cys-67-82 PC) (SEQ ID NO:2) were expressed in human embryonic kidney cells (HEK-293) by using the RSV-PL4 expression system purification vector system as described (Yang et al. (2006) Proc Natl Acad Sci. (USA); 103:879-884) and herein incorporated by reference. Two complementary sense 5'-AAG AAG CTC CTT GTC <u>TGC</u> CTT GGA GAG TAT GAC-3' (SEQ ID NO:3) and antisense 5'-GTC ATA CTC TCC AAG <u>GCA</u> GAC AAG GAG CTT CTT-3' (SEQ ID NO:4) oligonucleotide PCR primers representing the three base codons for the amino acid residues 62-72 (chymotrypsin numbering) were synthesized in which the codon for Arg-67 (residue 264 of SEQ ID NO:1) was replaced with the codon for cysteine in both primers (underlined). Moreover, two additional oligonucleotides 5'-GAG AAG TGG GAG CTG <u>TGC</u> CTG GAC ATC AAG GAG-3' (SEQ ID NO:5) (sense) and 5'-CTC CTT GAT GTC CAG <u>GCA</u> CAG CTC CCA CTT CTC-3' (SEQ ID NO:6) (anti-sense) representing amino acid residues 77-87 were synthesized in which the codon for the residue Asp-82 (residue 279 of SEQ ID NO:1) was replaced with the codon representing cysteine in both primers (underlined) The protein C cDNA (SEQ ID NO:7) (Accession number NM_000312) was amplified in two rounds to incorporate the desired mutations into the protein C sequence using standard PCR mutagenesis methods as previously described (Rezaie et al. (1992). Journal of Biological Chemistry, vol. 267, pp. 26104-26109) and herein incorporated by reference. The resulting mutant protein C cDNA (SEQ ID NO:8) was sub-cloned into HindIII and XbaI restriction enzyme cloning sites of the commercially available expression vector pRc/RSV (Invitrogen, San Diego, Calif.) using standard cloning methods. This vector contains a G418 resistant gene for selection in mammalian cells using the aminoglycoside antibiotics Gentamycin (Calbiochem, San Diego, Calif.). The accuracy of the mutations in the expression vector containing the mutant cDNA was confirmed by DNA sequencing and then introduced to human embryonic kidney (HEK) 293 cells for expression. A high expressing stable G418 resistant clone was identified by a Sandwich ELISA using an anti-protein C polyclonal antibody and the HPC4 monoclonal antibody, and expanded for production as described (Ref. Journal of Biological Chemistry, A. R. Rezaie and C. T. Esmon, vol. 267, pp. 26104-26109, 1992). The mutant protein (SEQ ID NO:2) was isolated from 20-L cell culture supernatants by a combination of immunoaffinity and ion exchange chromatography using the HPC4 monoclonal antibody and a Mono Q ion exchange column (Amersham Pharmacia).

Statistical Analysis

Results are expressed as mean ±SEM, and t-Tests (paired or independent) were used to assess data. Differences were considered statistically significant at p values of <0.05. Statistics were performed using the software package SPSS version 14.0 (SPSS, Chicago, Ill.).

Example 1

Protein C Activation by Thrombin

Protein C exists in the form of a zymogen and requires activation to exert its cytoprotective and anti-coagulant properties. Thrombin is a very poor activator of protein C in the absence of thrombomodulin (TM) (Esmon CT. (1993) Thromb. Haemost. 70:1-5). Activation of wild-type and cross-linked protein C (Cys-67-82) was compared to determine if the rate activation by free thrombin was increased.

The initial rate of protein C activation by thrombin was measured in 0.1 M NaCl, 0.02 M Tris-HCl, pH 7.4 (TBS) containing 1 mg/mL bovine serum albumin (BSA), 0.1% polyethylene glycol (PEG) 8000 and 2.5 mM $Ca^{2+}$ (TBS/Ca2+) in 96-well assay plates as described (Yang et al. (2006) Proc Natl Acad Sci. (USA); 103:879-884) and herein incorporated by reference. At different time intervals, thrombin activity was quenched by 500 nM AT in complex with 1 μM heparin. The activation rate was measured by an amidolytic activity assay using Spectrozyme PCa, and as described (Yang et al. (2006) Proc Natl Acad Sci. (USA); 103:879-884), the cleavage rate of 200 μM Spectrozyme PCa (American Diagnostica) was measured at 405 nm by a Vmax Kinetic Microplate Reader (Molecular Devices). The concentration of APC in the reaction mixture was determined by reference to a standard curve that was prepared by total activation of the zymogen with excess thrombin at the time of the experiments. All reactions were carried out at room temperature, and it was ensured that less than 10% substrate was used in all activation reactions.

Figure 2:
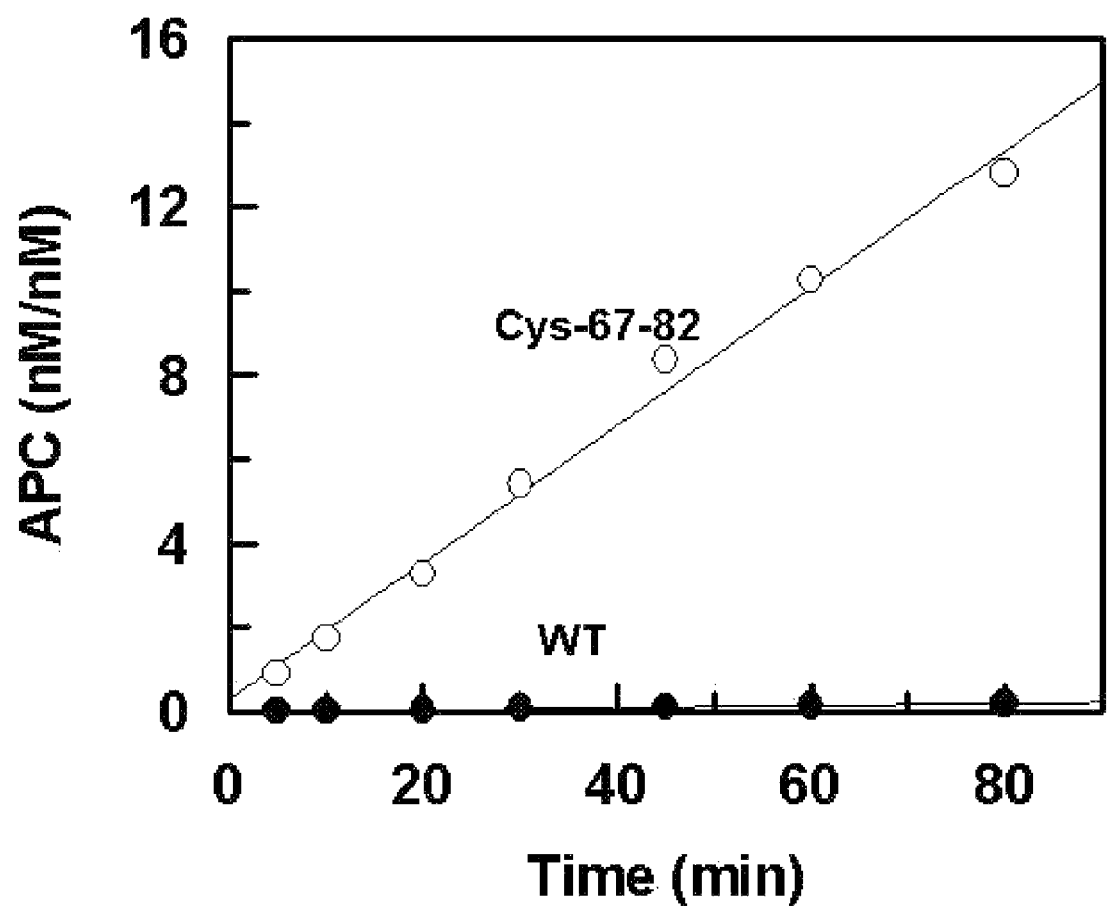
FIG. 2 illustrates protein C activation by thrombin. The activation of either wild-type (●) or Cys-67-82 protein C (cross-linked protein C) (○) (1 µM each) was monitored by thrombin (5-50 nM) in TBS/Ca2+ at room temperature. The rate of APC generation was determined by an amidolytic activity assay following thrombin neutralization by anti-thrombin. The activation rate was 0.002 nM and 0.16 nM APC/nM thrombin for wild-type and mutant protein C, respectively.

The initial rate of wild-type and mutant protein C activation by thrombin in the absence of TM and in the presence of physiological concentrations of $Ca^{2+}$ is presented in FIG. 2. Comparisons of the activation these rates suggest that, relative to wild-type, the activation of Cys-67-82 protein C by thrombin was improved 60-80-fold independent of TM.

The $Ca^{2+}$-dependence of protein C activation by thrombin revealed that the 70-80 loop of the mutant did not bind $Ca^{2+}$ (data not shown).

A benefit of this increased level of activation by thrombin is that cross-linked protein C may be more effective than wild-type protein C or other variants. When administered as a zymogen, cross-linked protein C will be activated on demand by endogenous free thrombin. This is particularly beneficial during inflammation conditions where TM on the endothelial cell surface is down regulated and less readily available. Under these conditions, wild-type or other variants will be activated less efficiently, and also will posses anti-coagulant properties that will increase the risk of severe bleeding.

Example 2

Anti-Coagulant Activity

The anti-coagulant activity of wild-type and Cys-67-82 APC was examined in purified and plasma-based clotting assays. In the purified system, APC concentration dependence of fVa inactivation was measured by a prothrombinase assay from a decrease in the fVa-catalyzed prothrombin activation as described (Yang et al. (2005) Thromb Haemostas.; 94:60-68). Essentially, fVa (5 nM) was incubated with wild-type or mutant APC (1 nM) on 25 μM PC/PS vesicles in TBS containing 2.5 mM Ca2+, 0.5 mg/ml BSA and 0.1% PEG 8000. In the second stage, at different time intervals (0-40 min), the remaining fVa activity was determined in a prothrombinase assay from the fVa-catalyzed prothrombin activation by fXa. The prothrombinase assay was carried out for 30 sec with excess prothrombin (1 µM) and a saturating fXa (10 nM) at room temperature. The remaining activity of fVa was determined from the decreased rate of thrombin generation as monitored by an amidolytic activity assay in the third stage using 100 µM S2238.

The anti-coagulant activities in plasma were evaluated in an activated partial thromboplastin time (APTT) assay using a STart 4 fibrinometer (Diagnostica/Stago, Asnieres, France) as described (Yang et al. (2005) Thromb Haemostas.; 94:60-68). Briefly, 0.05 ml TBS lacking or containing 1-20 nM final concentrations of wild-type or mutant APC was incubated with a mixture of 0.05 ml normal pooled plasma plus 0.05 ml APTT reagent (Alexin) for 5 min before the initiation of clotting by the addition of 0.05 ml of 35 mM $CaCl_2$ at 37° C.

Figure 3:
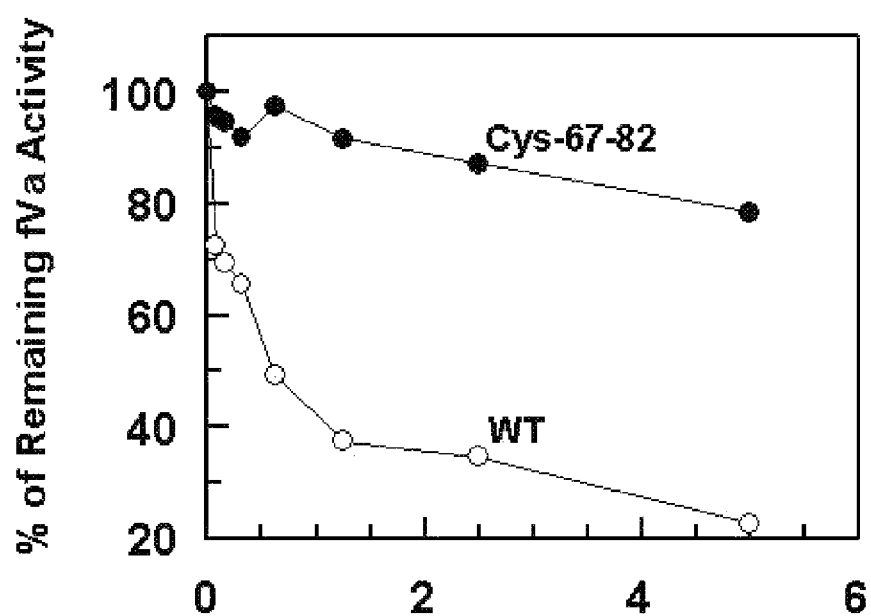
FIG. 3 illustrates the comparison of the anti-coagulant activity of wild-type and Cys-67-82 APC. (A) The rate of fVa degradation by either wild-type (○) or Cys-67-82 APC (●) was measured by a fVa-mediated thrombin generation assay. (B) the anti-coagulant activity of either wild-type (○) or Cys-67-82 APC (●) was measured in an activated partial thromboplastin time (APTT) assay.
Figure 3:
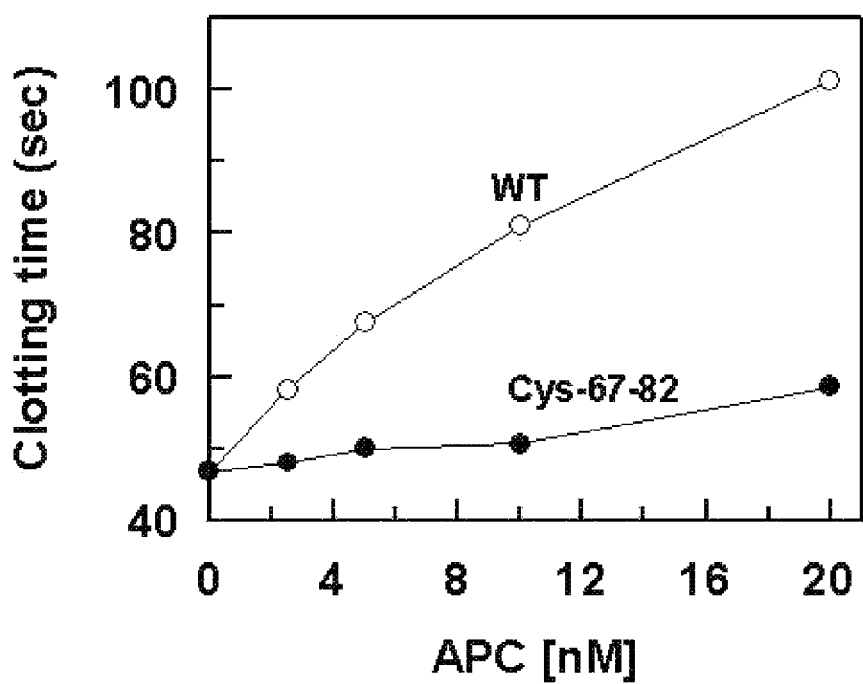

As presented in FIG. 3A, Cys-67-82 APC exhibited dramatically impaired activity in a fVa degradation assay monitoring the inhibition of thrombin generation by prothrombinase. Similarly, in the APTT initiated clotting assay, the APC mutant did not exhibit any anti-coagulant activity for up to 10 nM protease and doubling the concentration of the mutant minimally improved the specific activity of the protease in the clotting assay (FIG. 3B). The lack of anti-coagulant activity for the cross-linked APC was not due to its enhanced reactivity with plasma serpins, as evidenced by a normal inhibition profile for the mutant with anti-thrombin, α1-antitrypsin and protein C inhibitor (data not shown). This was confirmed by direct monitoring of the time course of the amidolytic activity of wild-type and mutant APC following incubation with normal plasma (data not shown). Therefore, it was demonstrated that Cys-67-82 APC did not readily prevent clot formation. This would indicate that unlike wild type APC, the risk of enhanced bleeding would not occur with administration of Cys-67-82 APC.

Example 3

Effect of APC on Thrombin-induced Permeability

It is known that thrombin disrupts the permeability barrier of endothelial cells, thereby further propagating the inflammatory response. It is also known that APC provides potent protection against these effects (Feistritzer et al. (2005) Blood.; 105:3178-3184). To determine whether Cys-67-82 APC retained this protective property, an assay was designed to compare the protective effect of Cys-67-82 APC with that of the wild-type APC.

Permeability was quantitated by spectrophotometric measurement of the flux of Evans blue-bound albumin across functional EA.hy926 cell monolayers using a modified 2-compartment chamber model as previously described (Feistritzer et al. (2005) Blood.; 105:3178-3184). Briefly, EA.hy926 cells were plated ($5 \times 10^4$/well) in transwell of 3 µm pore size and 12-mm diameter for 4-6 days. The confluent monolayers were incubated with APC (20 nM) for 3 h followed by activation by thrombin (5 nM) for 10 min as described (Feistritzer et al. (2005) Blood.; 105:3178-3184). Inserts were washed with PBS, pH 7.4 before adding 0.5 mL Evans blue (0.67 mg/mL) (Sigma, St Louis, Mo.) diluted in growth medium containing 4% BSA. Fresh growth medium was added to the lower chamber, and the medium in the upper chamber was replaced with Evans blue/BSA. After 10 min the optical density at 650 nm was measured in the lower chamber. For the function-blocking antibody treatments of the monolayers, medium was removed and antibodies were added for 30 min in serum-free medium followed by analysis of the permeability. Experiments were performed in triplicate and repeated multiple times.

Figure 4:
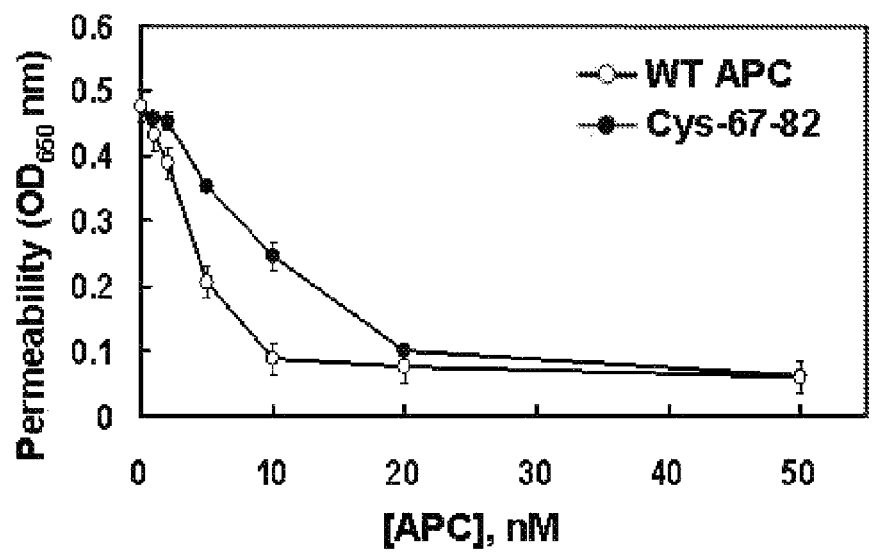
FIG. 4 illustrates thrombin-induced permeability in EA.hy926 cells. (A) The concentration of APC (○ wild-type APC, ● Cys-67-82 APC) dependence of the inhibition of thrombin-induced permeability was monitored from the flux of Evans blue-bound albumin across confluent EA.hy926 cells. (B) Permeability was quantitated (*p<0.005) in the absence and presence of function-blocking antibodies to either EPCR or PAR-1 (H-111). S-19 is a non-function-blocking antibody to PAR-1.
Figure 4:
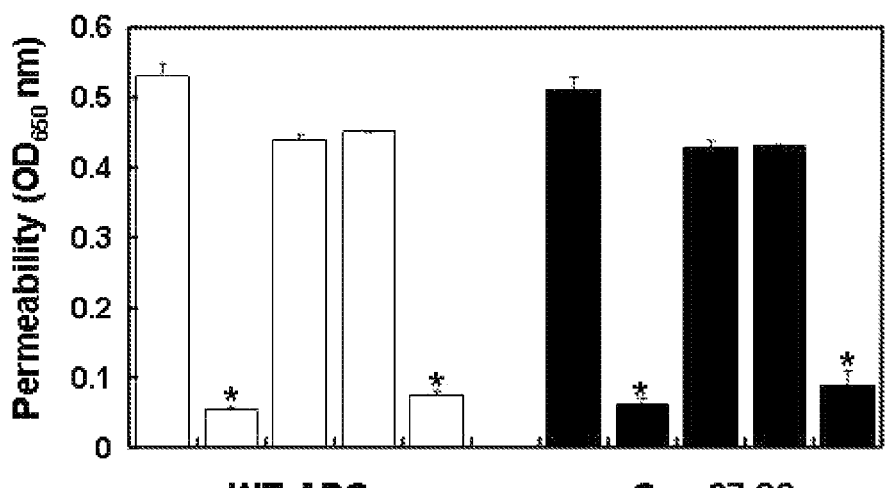

As shown in FIG. 4, treatment of EA.hy926 cells with thrombin resulted in an enhanced permeability that was effectively reversed by both wild-type and Cys-67-82 APC. In agreement with published data for APC, (Feistritzer et al. (2005) Blood.; 105:3178-3184) the protective effect of the APC mutant required the interaction of the protease with both EPCR and PAR-1. This was demonstrated using function-blocking antibodies to either EPCR or PAR-1 (H-111). When these antibodies were included, the protective effects of both wild-type and Cys-67-82 APC were eliminated (FIG. 4B). S-19 is a non-function-blocking antibody against PAR-1, which was used as a control. These results indicate that Cys-67-82 APC has retained this protective property and functioned through the same signaling pathways. Comparisons of concentration dependence of the cytoprotective activity of wild-type and mutant APC suggested that, slightly more, 10 nM cross-linked APC compared to 5 nM wild-type APC, was required to obtain a maximal cytoprotective effect (data not shown).

Example 4

Anti-apoptotic Activity of APC

The anti-apoptotic effects of Cys-67-82 APC were demonstrated in endothelial cells under conditions known to induce apoptosis.

Apoptotic effects were determined by measuring known apoptotic indicators, Bcl-2 p53, Bax and AIF genes, and Terminal deoxynucleotidyl Transferase Biotin-dUTP Nick End Labeling (TUNEL). The transformed human endothelial cell line EA.hy926 were cultured to confluence in a humidified atmosphere at 37° C. in Dulbecco modified eagle medium (Invitrogen, Carlsbad, Calif.) supplemented with 10% fetal bovine serum (HyClone, Logan, Utah) and antibiotics (penicillin G and streptomycin). EA.hy926 cells (0.5× 106) were seeded onto coverslips coated with gelatin as described. (Mosnier et al. (2003) Biochem J.; 373:65-70). After 24 h at 37° C., the medium was replaced and cells were incubated with protein C or APC (10 nM) for another 24 h. Then, the cells were incubated with 5 µM staurosporine for 4 h. The cells were fixed with 3% paraformaldehyde, permeabilized with 0.1% Triton X-100, 0.1% sodium citrate, and incubated for one h at 37° C. in the dark with a TUNEL reaction mixture (Roche, Germany) for in situ detection of cell death. After twice washing with PBS pH 7.4, the cells were incubated with the Hoechst 33342 (Sigma, St Louis, Mo.) for 15 min. The number of apoptotic cells was expressed as the percentage of TUNEL-positive cells of the total number of nuclei determined by Hoechst staining.

Figure 5A:
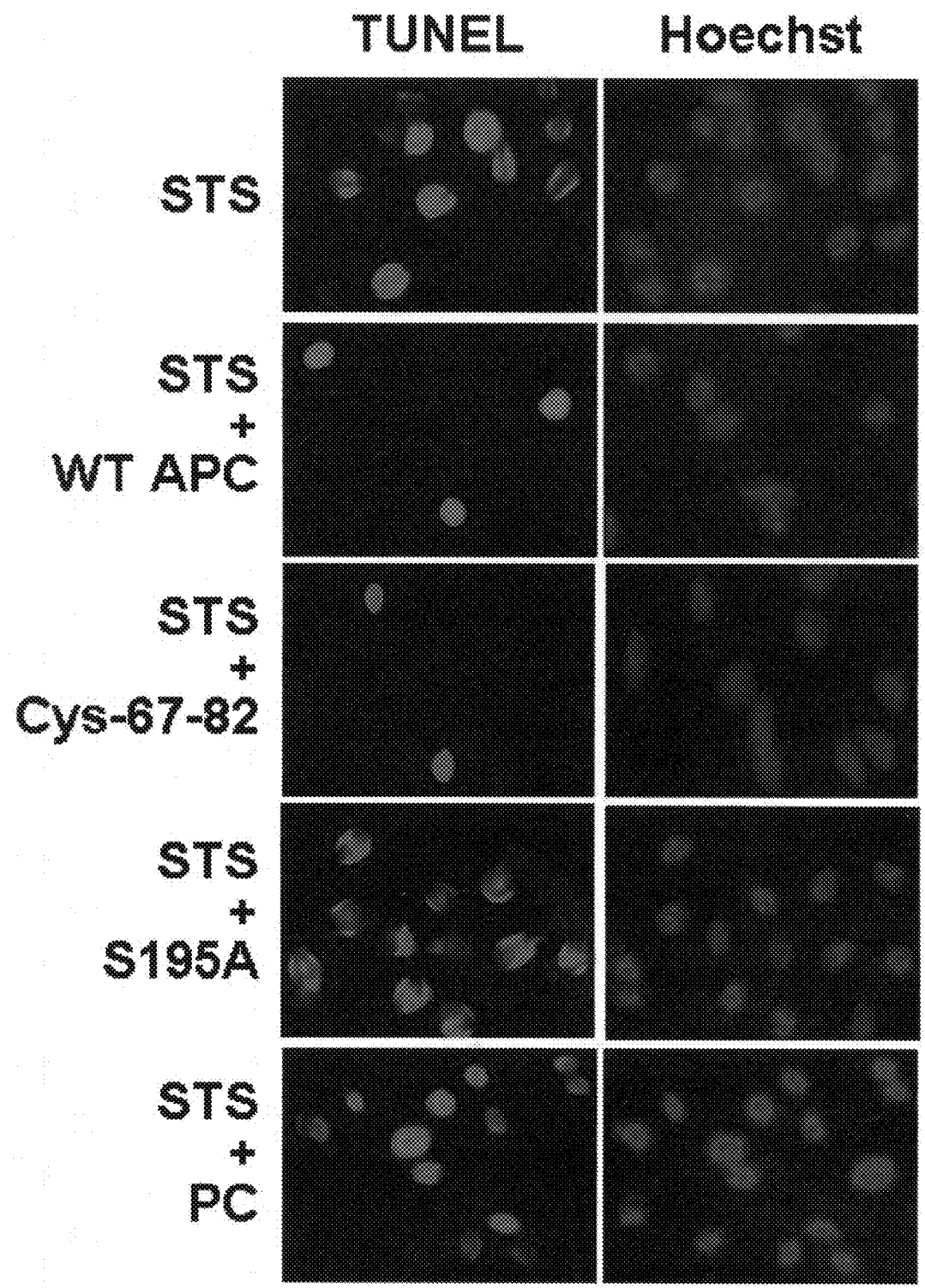
FIG. 5 illustrates the anti-apoptotic activity of APC in the staurosporine-induced apoptosis assay. (A) Confluent monolayers of EA.hy926 cells were treated with APC derivatives (10 nM) for 24 h followed by induction of apoptosis with staurosporine (STS=5 μM) for 4 h. The cells were fixed with paraformaldehyde and incubated with the TUNEL reaction mixture followed by Hoechst 33342 to stain the apoptotic cells (green) and the total number of nuclei (blue), respectively. (B) The number of apoptotic cells was expressed as the percentage of TUNEL-positive cells of the total number of nuclei (*p<0.001). (C) Western-blot analysis of the total cellular proteins developed with the indicated antibodies using standard methods.
Figure 5:
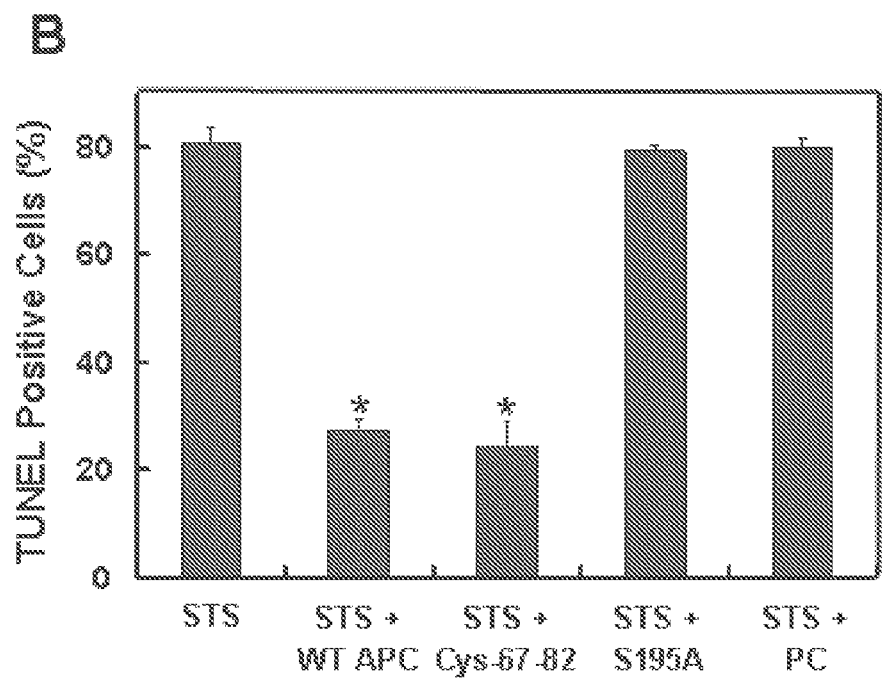
Figure 5:
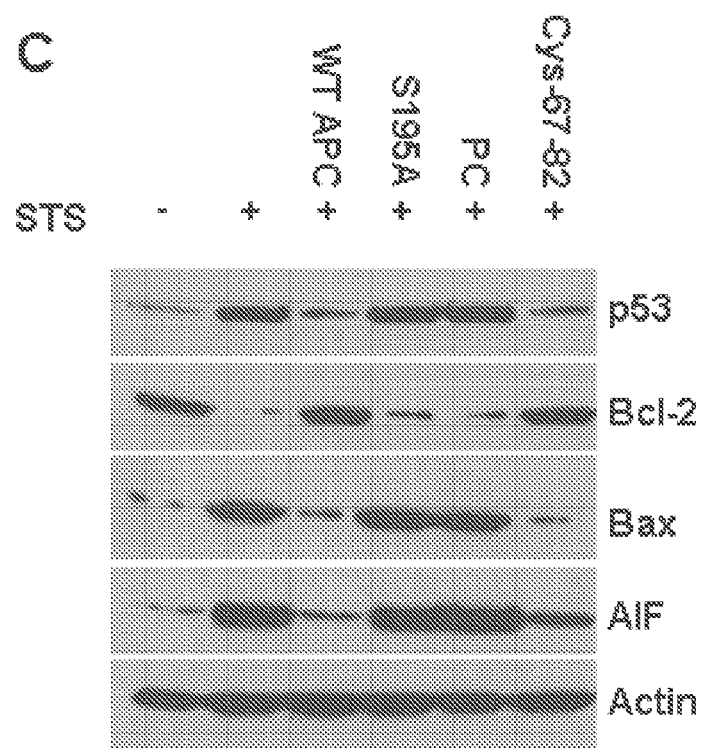

Previous results have demonstrated that APC exhibits cytoprotective activity in a staurosporine-induced apoptosis assay (Mosnier et al. (2003) Biochem J.; 373:65-70). As shown in FIG. 5, the APC mutant exhibited normal anti-apoptotic activity in EA.hy926 cells treated with staurosporine. The cytoprotective activity of both APC derivatives were mediated, at least partially, through inhibition of the caspase-3 activity and the function-blocking antibodies to either EPCR or PAR-1 abrogated the anti-apoptotic activity of both APC derivatives (data not shown). The cytoprotective activity of APC required an intact active-site and was mediated through the up-regulation of Bcl-2 and the down-regulation of p53, Bax and AIF genes (FIG. 5C) as previously demonstrated.

Figure 6A:
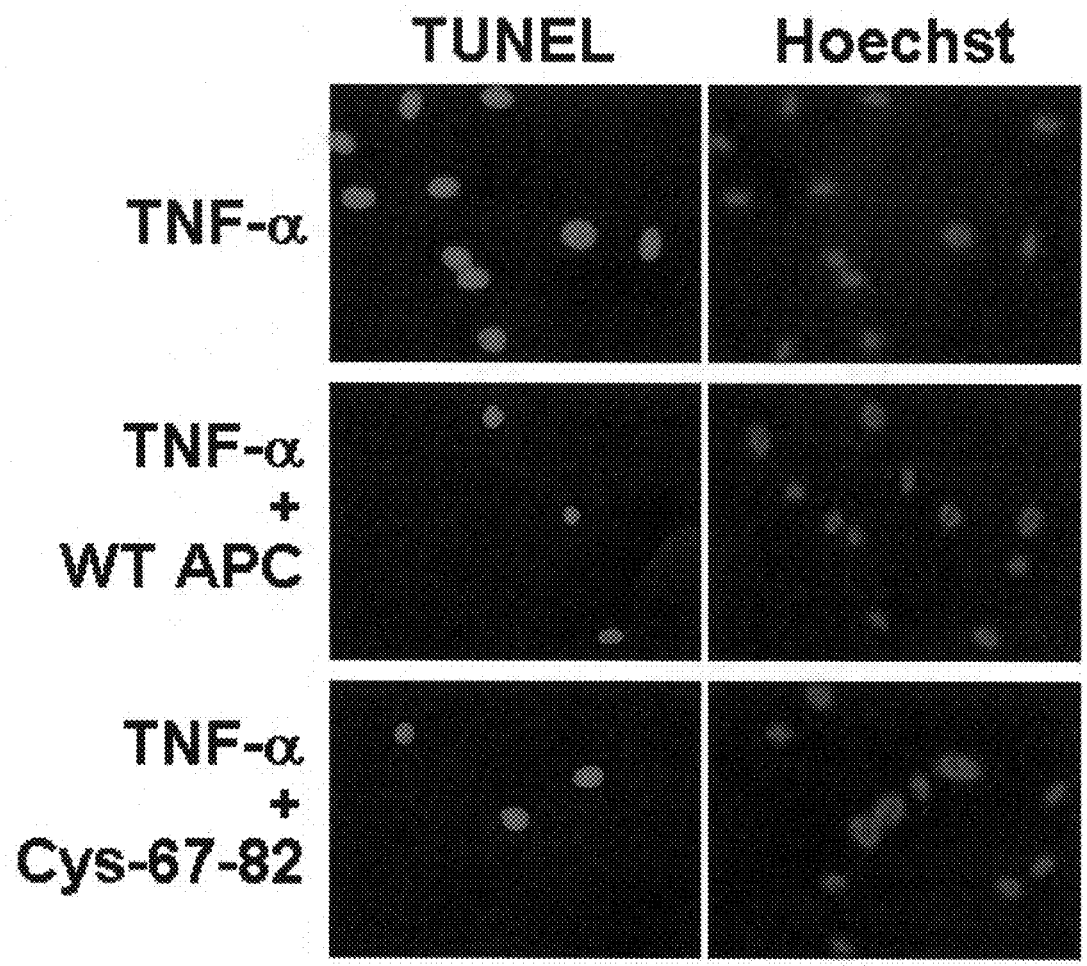
FIG. 6 illustrates the anti-apoptotic activity of APC derivatives in the TNF-α-induced apoptosis assay. Conditions are the same as in FIG. 5 except that TNF-α (10 ng/mL) was used to induce apoptosis (*p<0.001).
Figure 6B:
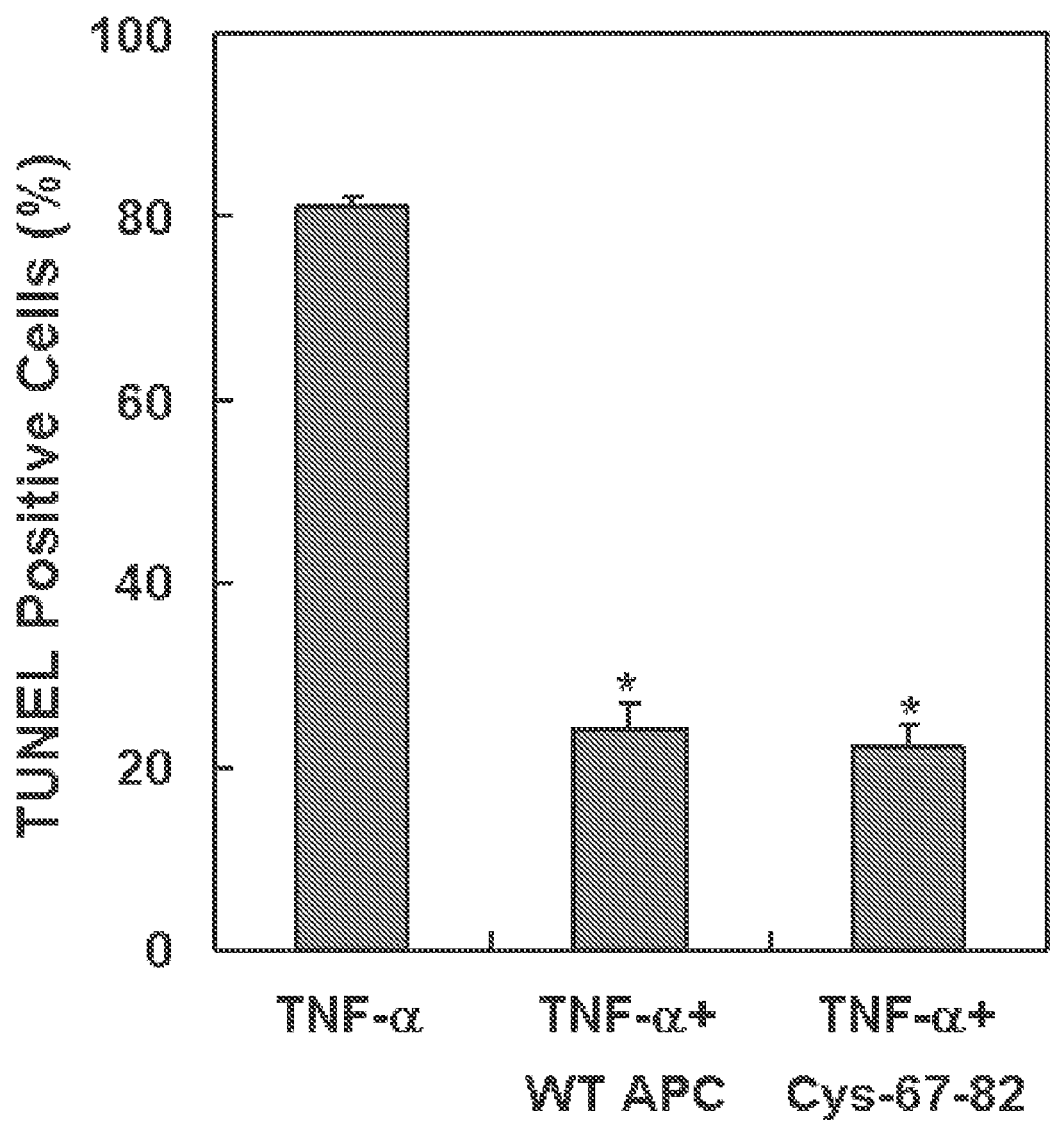

(Oren M. (1999) J Biol Chem.; 274:36031-36034; Cheng et al. (2003) Nature Med.; 9:338-342; Guo et al. (2004) Neuron.; 41:563-572). These studies were extended to examine whether APC can also inhibit apoptosis in TNF-α-treated EA.hy926 cells. As shown in FIG. 6, TNF-α treatment of confluent endothelial cells induced an apoptotic pathway that was detected by a TUNEL assay. The pretreatment of endothelial cells with 10 nM of either wild-type or mutant APC potently inhibited cell death induced by TNF-α (FIG. 6B). Therefore, it was demonstrated that Cys-67-82 APC possessed anti-apoptotic properties.

Example 5

Effect of APC on TNF-α-Mediated Leukocyte Adhesion and Migration

To further understand the anti-inflammatory and anti-apoptotic properties of Cys-67-82 APC, expression of cell adhesion molecules (CAM), as well as the adherence and migration of neutrophils on endothelial cells was examined.

Neutrophil adherence to endothelial cells was evaluated by fluorescent labeling of neutrophils according to the methods of Akeson and Woods as described (Akeson et al. (1993) J Immunol Methods.; 163:181-185; Kim et al. (2001) J Biol Chem.; 276:7614-7620). Briefly, peripheral blood neutrophils were labeled with 5 µM Vybrant DiD (Molecular Probes) for 20 min at 37° C. in phenol red-free RPMI containing 5% fetal bovine serum. Following twice washing of neutrophils ($1.5 \times 10^6$/ml, 200 µl/well), they were resuspended in adhesion medium (RPMI containing 2% fetal bovine serum and 20 mM HEPES) and added to confluent monolayers of EA.hy926 cells in 96-well plates which were treated with APC derivatives (20 nM for 24 h) followed by activation by TNF-α (10 ng/mL) for 4 h. The fluorescence of labeled cells was measured (total signal) using a fluorescence microplate reader (Molecular Device). After incubation for 60 min at 37° C., non-adherent cells were removed by washing four times with pre-warmed RPMI and the fluorescent signals of adherent cells were measured by the same methods. The percentage of adherent leukocytes was calculated by the formula:

% adherence=(adherent signal/total signal)×100.

The expression of vascular cell adhesion molecule 1 (VCAM-1), intercellular adhesion molecule 1 (ICAM-1) and E-selectin on EA.hy926 cells was determined by a whole-cell ELISA. Briefly, confluent monolayers of EA.hy926 cells were treated with APC derivatives (20 nM) for 24 h followed by TNF-α for 4 h. The medium was removed; cells were washed with PBS, and fixed by adding 50 µL of 1% paraformaldehyde for 15 minutes at room temperature. After washing, 100 µL of mouse anti-human monoclonal antibodies (VCAM-1, ICAM-1, E-selectin, Temecula, Calif., 1:50 each) were added. After 1 h (37° C., 5% CO2), the cells were washed three times and then 100 µL of 1:2000 peroxidase-conjugated anti-mouse IgG antibodies (Sigma, Saint Louis, Mo.) was added for 1 h. The cells were washed again three times and developed using o-phenylenediamene substrate (Sigma, Saint Louis, Mo.). Colorimetric analysis was performed by measuring absorbance at 490 nm. All measurements were performed in triplicate wells.

Migration assays were performed in transwell plates of 6.5 mm diameter, with 8 µm pore size filters. EA.hy926 cells ($6 \times 10^4$) were cultured for three days to obtain confluent endothelial monolayers. Before adding neutrophils to the upper compartment, the cell monolayers were washed three times with PBS, and freshly isolated neutrophils ($1.5 \times 10^6$/0.2 mL) were added to the upper compartment. In blocking experiments, the EA.hy926 cells were preincubated for 30 min at 37° C. with indicated antibodies. Transwell plates were incubated at 37° C., 5% $CO_2$ for 2 h. Cells in the upper chamber of the filter were aspirated and non-migrating cells on top of the filter were removed with a cotton swab. Neutrophils on the lower side of the filter were fixed with 8% glutaraldehyde and stained with 0.25% crystal violet (Sigma, St Louis, Mo.) in 20% methanol (w/v). Each experiment was repeated in duplicate wells and within each well counting was done in nine randomly selected microscopic high power fields.

Figure 7A:
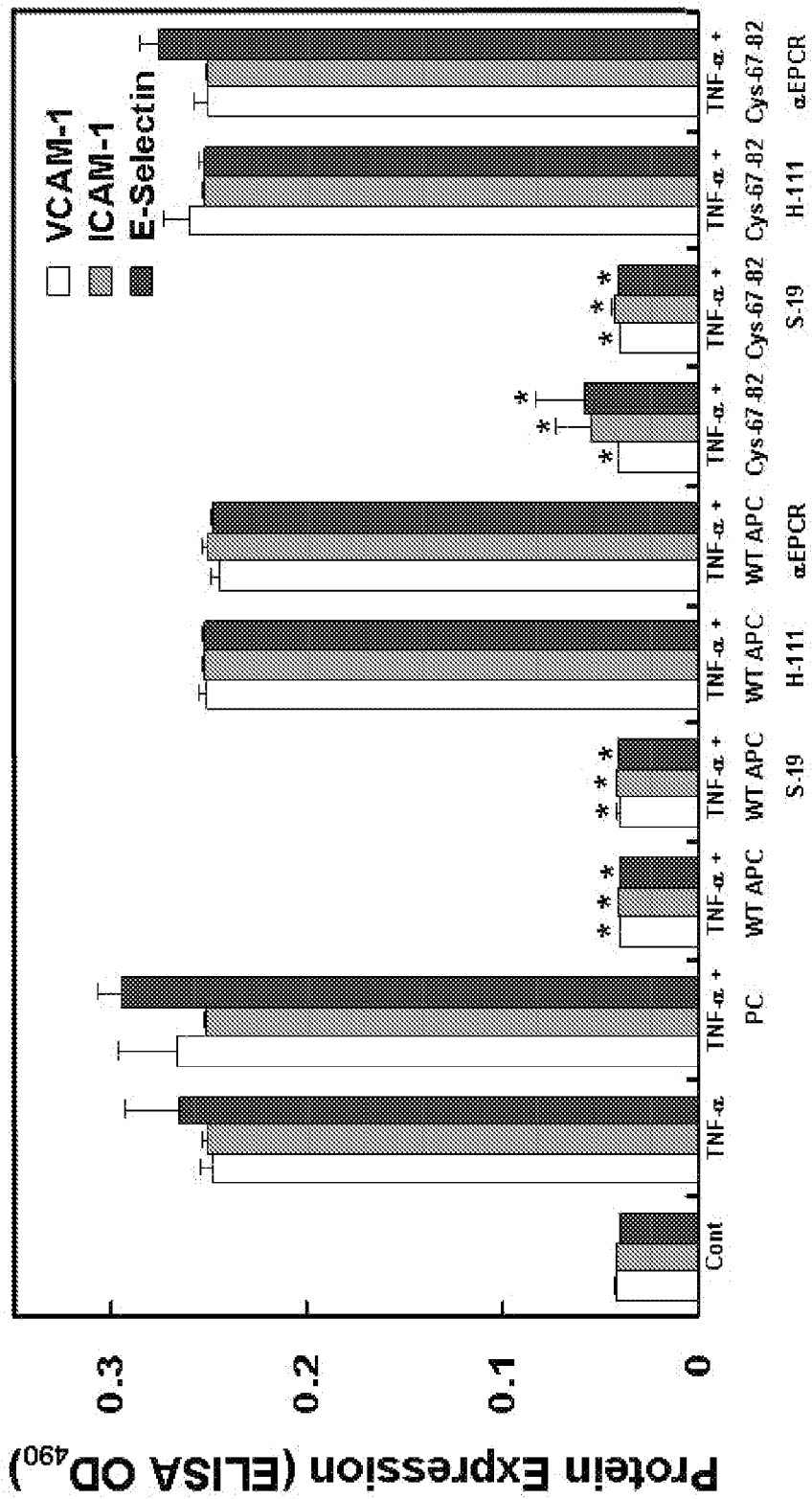
FIG. 7 illustrates the TNF-α-induced adhesion and transendothelial migration of neutrophils in EA.hy926 cells. (A) TNF-α-mediated (10 ng/mL) expression of adhesion molecules in EA.hy926 cells was analyzed after treating monolayers with protein C (PC), APC, or Cys-67-82 APC (20 nM each) in the absence and presence of function-blocking antibodies to EPCR and PAR-1 (H-111) or non-blocking antibody to PAR-1 (S-19). (B) TNF-α-mediated adherence of neutrophils to EA.hy926 monolayers was analyzed after treating monolayers with protein C (PC), APC S195A, APC, or Cys-67-82 APC in the absence and presence of the same antibodies in panel A. (C) The same as B except that transendothelial migration of neutrophils was analyzed as described under "Materials and Methods for Examples". *p<0.001 in all three panels.
Figure 7B:
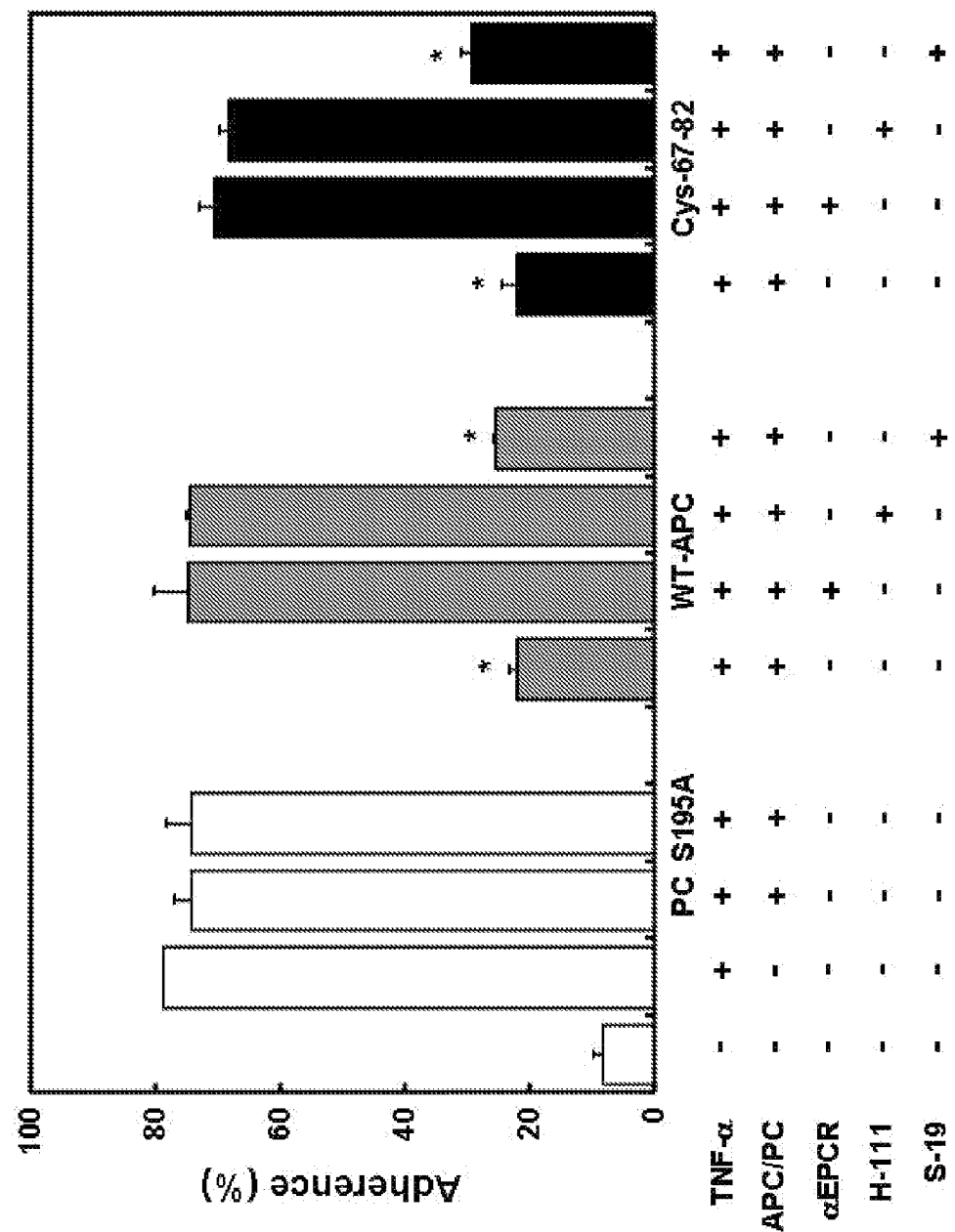
Figure 7C:
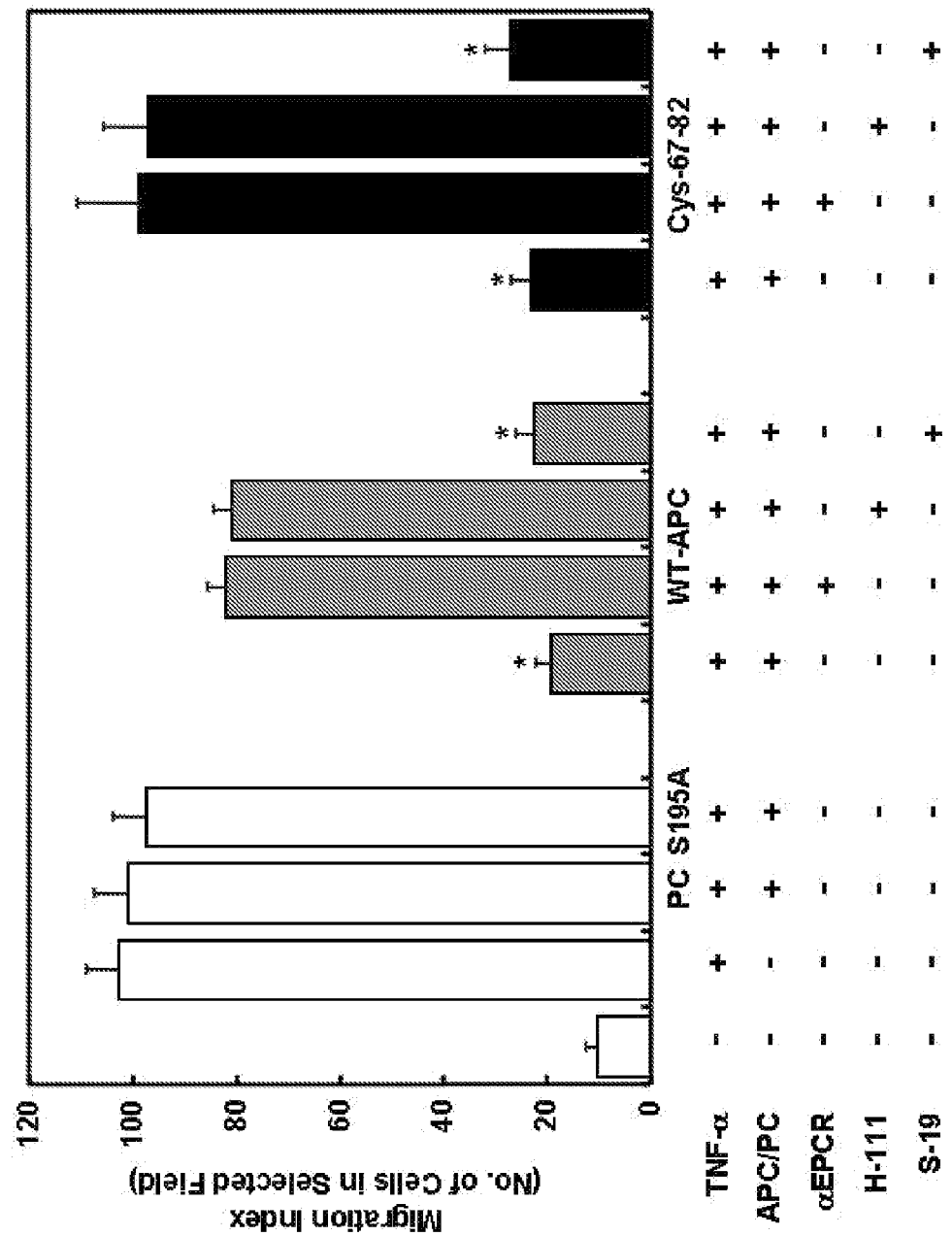

The TNF-α treatment of HUVECs is associated with the up-regulation of several cell surface adhesion molecules such as VCAM-1, ICAM-1 and E-selectin and APC has been demonstrated to inhibit the expression of these molecules. (Joyce et al. (2001) J Biol Chem.; 276:11199-11203). The results presented in FIG. 7A support these findings in EA.hy926 cells and further demonstrate that APC suppression of the TNF-α-mediated expression of adhesion molecules is EPCR and PAR-1-dependent as evidenced by the ability of the function-blocking antibodies to either receptor to neutralize the modulatory effect of APC. Similar to wild-type, the APC mutant down-regulated the TNF-α-mediated expression of all three adhesion molecules in EA.hy926 cells (FIG. 7A). Further studies were initiated to determine whether the expression of these adhesion molecules correlates with enhanced binding of neutrophils and if APC can block the adhesion of neutrophils to TNF-α-activated EA.hy926 cells. The results presented in FIG. 7B demonstrate that both APC derivatives effectively inhibited the binding of neutrophils to the TNF-α-activated endothelial cells by EPCR and PAR-1-dependent pathways. Further studies revealed that the adhesion of neutrophils to endothelial cells is associated with their subsequent transendothelial migration and that both APC derivatives inhibit this step by a similar EPCR and PAR-1-dependent mechanism (FIG. 7C). Moreover, the inhibition of neutrophil transendothelial migration required proteolytic events by APC since neither protein C nor S195A PC exhibited any inhibitory property (data not shown). Therefore Cys-67-82 APC will inhibit the binding of neutrophils to endothelial cells under conditions that induce inflammation or apoptosis.

Taken together, Examples 1-5 clearly demonstrate that, unlike the near complete loss of the anti-coagulant activity, the in vitro indices of the anti-inflammatory and cytoprotective activities of the APC mutant have remained intact including the endothelial protein C receptor (EPCR), and protease-activated receptor-1 (PAR-1) dependent signaling properties. These results indicate that the modulation of the structure and/or activity of the catalytic domain of the APC 70-80 loop may be required for its anti-coagulant, but not for its anti-apoptotic properties. The anti-coagulant function of APC may require the cofactor functions of the metal ions $Ca^{2+}$ and $Na^+$ both of which allosterically modulate the structure and catalytic function of APC (He et al. (1999) J Biol Chem.; 274:4970-4976). Such a coordinated metal ion modulation of the APC structure and function has been disrupted in cross-linked APC since the engineered disulfide bond may abolishes the requirement for $Ca^{2+}$ and may stabilizes the $Na^+$ binding site of the mutant protease in the high affinity state. These structural changes may be important for the anti-coagulant function but not for the protective signaling effects of APC.

For APC to elicit protective signaling responses, it must remain associated with EPCR on the surface of endothelial cells. The exact mechanism through which APC exerts its cell signaling effects is not known. In vitro and in vivo studies have demonstrated that, in addition to binding EPCR, the protective signaling effect of APC also requires the presence of PAR-1 on the surface of endothelial cells (Feistritzer et al. (2005) Blood.; 105:3178-3184; Cheng et al. (2003) Nature Med.; 9:338-342).

Studies have indicated that the EPCR-dependent cleavage of PAR-1 at Arg-41, the same recognition site on the receptor for thrombin (Coughlin S R. (1994) Trends Cardiovasc Med.; 4:77-83), is responsible for the direct cell signaling effect of APC (Mosnier et al. (2004) Blood. 104:1740-1744). Studies have also shown that APC down-regulates expression of several key pro-inflammatory cytokines (i.e., TNF-α and IL-1), adhesion molecules (i.e., ICAM-1 and VCAM-1), and transcription factors (i.e., nuclear factor-kB related molecules) in human endothelial and non-endothelial cells (9).

Cross-linked APC retains these anti-inflammatory and anti-apoptotic properties. Both wild-type and cross-linked APC inhibited the TNF-α-mediated up-regulation of ICAM-1, VCAM-1, and E-selectin. Typically, during an inflammatory response the expression of these adhesion molecules is up regulated. Leukocytes undergo extravasation by binding to these molecules on the surface of endothelial cells (Kim et al. (2001) J Biol Chem.; 276:7614-7620). As disclosed herein, it was demonstrated that the enhanced TNF-α-mediated expression of these adhesion molecules on transformed endothelial cells is associated with increased binding of neutrophils and their subsequent transendothelial migration. Cross-linked APC has effectively inhibited these processes through EPCR and PAR-1-dependent mechanisms.

Increased vascular permeability is another hallmark of inflammatory disorder, and has been observed during sepsis (Finigan et al. (2005) J Biol Chem.; 280:17286-17293). In vitro studies have shown that APC reverses thrombin-induced endothelial permeability. This effect is responsible for enhancing the anti-inflammatory properties of APC and improving survival in severely septic patients (Finigan et al. (2005) J Biol Chem.; 280:17286-17293; Feistritzer et al. (2005) Blood.; 105:3178-3184). Cross-linked APC exhibits normal protective endothelial barrier properties via EPCR and PAR-1-dependent mechanisms. Also, as demonstrated using a staurosporine-induced apoptosis assay, the cytoprotective properties of the cross-linked APC are normal and mediated through the inhibition of caspase 3, up-regulation of Bcl-2, and down-regulation of p53, Bax, and AIF genes as previously shown for wild-type APC. (Mosnier et al. (2004) Blood. 104:1740-1744; 29, 30) Using this assay, it was demonstrated that cross-linked APC functioned by similar EPCR and PAR-1-dependent mechanisms. In addition, the anti-apoptotic activity of cross-linked APC using the pro-inflammatory cytokine TNF-α to induce apoptosis in endothelial cells was also evaluated. It was found that similar to wild-type, cross-linked APC potently inhibited cell death induced by the physiological cytokine TNF-α.

Example 6

Anti-coagulant Activity of Cys-67-82 APC in Baboon and Mouse Plasma

Figure 8:
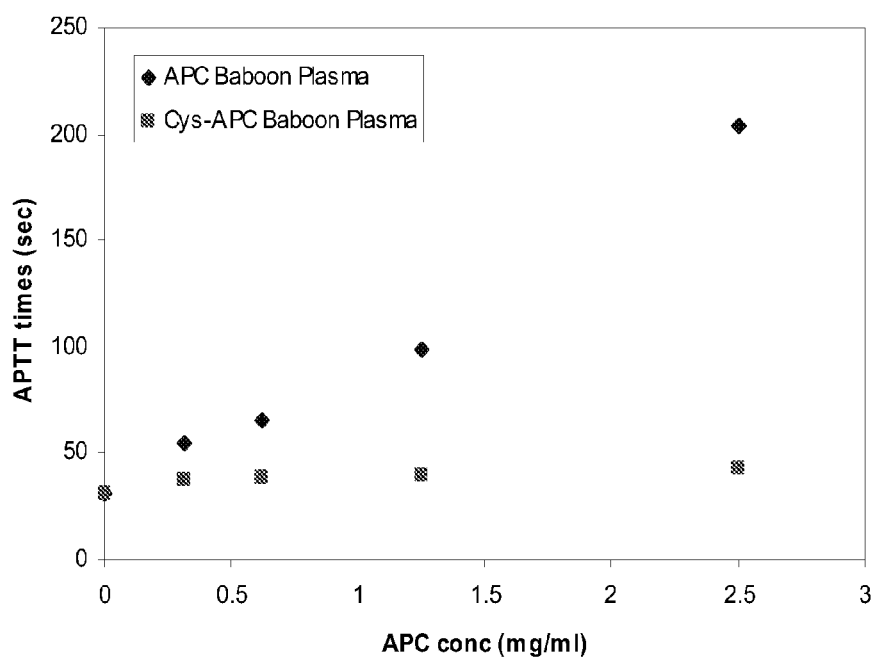
FIG. 8 illustrates the anticoagulant effects of WT APC and Cys-67-82 APC (Cys APC) in the APTT in baboon (A) and mouse (B) plasma. Compared to wild-type APC Cys-67-82 APC was seen to have potent anti-coagulant effects in both baboon and mouse plasma.
Figure 8:
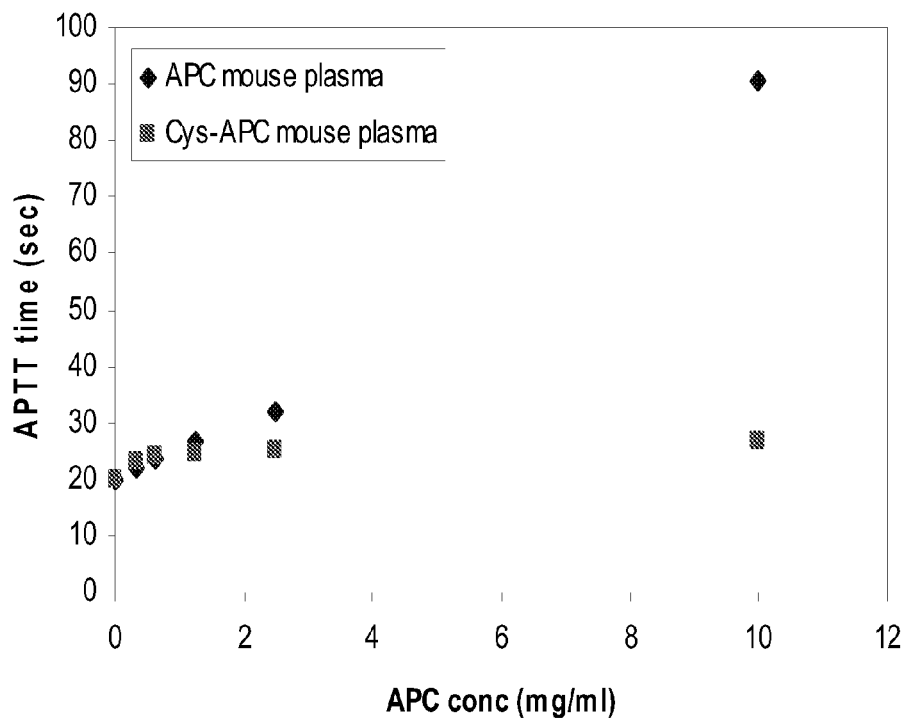

In preparation for studies in vivo, the inventors investigated the effects of Cys-67-82 APC on coagulation time in baboon and mouse plasma in vitro. The methodology used is described in Example 2 for human plasma. Compared to WT APC, Cys-67-82 APC demonstrated greatly reduced anti-coagulant activity in both baboon and mouse plasma, in the APTT tests (Cys APC, FIG. 8). These results were similar to those obtained using pooled human plasma (see Example 2). Similarity anticoagulant properties between species, suggested that the baboon and mouse models would also be suitable to demonstrate the protective behaviors of Cys-67-82 APC in vivo.

Example 7

Anti-thrombotic and Anti-hemostatic Activities of Cys-67-82 APC in Primates

Experiments were designed to determine whether Cys-67-82 APC exhibits anti-thrombotic and anti-hemostatic effects in a primate model of hemostasis. All experiments were performed using trained conscious baboons with surgically implanted chronic arteriovenous shunts, essentially as described (Hanson 1993, Gruber 2007). In brief, a thrombogenic device consisting of a 20 mm long knitted polyethylene terephthalate (Dacron) graft segment (4 mm ID) and a 20 mm long silicone rubber thrombus chamber (9 mm ID) was deployed into the shunt at 0 min and perfused for one hour at a controlled blood flow rate of 100 mL/min. Fibrin deposition in the thrombogenic device, template bleeding times, and systemic APTT values were monitored. For the initial experiments, the inventors chose to compare the anti-thrombotic and anti-hemostatic effects of equal doses of WT and Cys-67-82 APC. Vehicle (N=6), WT APC(N=4), or Cys-67-82 APC(N=3) were administered as a loading bolus (75 µg/kg) at 0 min (start of experiment, immediately after deployment of the thrombogenic graft) followed by continuous infusion at a rate of 150 µg/kg/h. The results of the measurements were averaged but statistics were not provided due to the low number of experiments.

This model has been shown to be sensitive to numerous anti-thrombotic agents, including fibrinolytic agents, anticoagulants, and antiplatelet agents. End-point fibrin deposition in the thrombus chamber averaged 2.1 mg in controls, 2 mg after Cys-67-82 APC administration and 1 mg after WT APC treatment, indicating that the mutant APC demonstrated a reduced anti-thrombotic effect. Cys-67-82 APC also did not seem to have a profound affect on two hemostatic parameters, APTT and template bleeding time (Table 1).

TABLE 1

Hemostatic parameters in baboons during treatment with Cys-67-82 APC (CysAPC).

| Sampling time | APTT, sec CysAPC | APTT, sec WT APC | Bleeding time prolongation vehicle | Bleeding time prolongation WT APC | Bleeding time prolongation CysAPC |
|---|---|---|---|---|---|
| 0 min | 34.4 | 26.4 | | | |
| 10 min | 34.6 | 68.8 | | | |
| 40 min | 34.6 | 57.3 | 1.1-fold | 1.5-fold | 1.2-fold |
| 70 min | 34.4 | 57.1 | | | |

These results indicate that Cys-67-82 APC has reduced anti-coagulant effects in vivo compared to wild-type APC. In particular end-point fibrin deposition was increased compared to wild-type APC indicating reduced anti-coagulant activity.

Example 8

Neuroprotective Activities of Cys-67-82 APC in Mice

To examine the neuroprotective effects of Cys-67-82 APC on ischemia stroke, a mouse middle cerebral artery occlusion (MCAO) and reperfusion model was used. A mouse middle cerebral artery occlusion (MCAO) and reperfusion model was used essentially as described (Clark 1977), and modified (Choudri 1998, 1999, Shibata 2001). Isoflurane anesthesia was used during all invasive procedures. The femoral vein was aseptically isolated and soaked with sterile saline. A transcranial laser Doppler flow probe was secured in over the parietal lobe for blood flow monitoring of the cerebral cortex. Stroke was initiated in the right hemisphere by the MCAO procedure. Arterial stenosis, blood vessel injury, and secondary local activation of the coagulation cascade were initiated by temporary surgical deployment of a foreign body (6-0 nylon filament) into the middle cerebral artery (MCA) for 60 min. The beginning of cerebral ischemia was arbitrarily defined as decrease in blood flow over the parietal cortex below 20% of the pre-MCAO baseline. The intraluminal filament restricted blood flow to the ipsilateral hemisphere, initiated progressive thrombosis, and caused ischemic stroke in the MCA region. Treatments (see Table 2) were administered into the femoral vein while the filament was in the MCA. Infusion of the test agents started at 15 min from the beginning of cortical ischemia.

Measurements of cerebral infarction volumes were determined as follows. After 24 h, animals were killed and their brains rapidly harvested. Infarct volumes were determined by staining serial cerebral sections with triphenyltetrazolium chloride (TTC) and performing computer-based planimetry of the negatively stained areas to calculate infarct volumes (using National Institutes of Health image software).

Neurological exams were determined as follows. Before administering anesthesia, mice were examined for neurological deficits 23 h after reperfusion. Neurological scores were determined using a four-tiered grading system: a score of 1 was given if the animal demonstrated normal spontaneous movements; a score of 2 was given if the animal was noted to be turning towards the ipsilateral side; a score of 3 was given if the animal was observed to spin longitudinally (clockwise when viewed from the tail); and a score of 4 was given if the animal was unresponsive to noxious stimuli.

This model has been shown to be sensitive to all tested anti-thrombotic treatments, including high doses of APC and tPA (Shibata et al. (2001) Circulation. 103(13):1799-805; Fernandez et al. (2003) Blood Cells Mol Dis. (3):271-6; Kilic et al. (1999) Neuroreport, 10(1):107-11). Anti-thrombotic interventions reduce infarct size, improve neurological outcome, and improve blood flow recovery (reperfusion) in the affected brain region. This is a complex model that involves numerous connected events, and accordingly it is also sensitive and responsive to various other non-causal interventions, including, among others, the use of anti-apoptotic agents, temperature control, or post-ischemic care (McCullough et al. (2003) J Neurosci; 23(25):8701-5; Barber, et al. (2004) Stroke. 35(7):1720-5. Epub; DeVries et al. (2001) Proc Natl Acad Sci USA. 98(20):11824-8. Epub). The apparent neuroprotective effect of high dose WT human and mouse APC might be closely related to the catalytic activation of PAR1 and 3 (Guo et al. (2004) Neuron.; 41(4):563-72; Domotor et al. (2003) Blood.; 101(12):4797-801. Epub; Cheng, et al. (2003) Nat Med. 9(3):338-42. Epub), and protection of the neurovascular unit from ischemia and/or reperfusion injury.

Preliminary experiments were performed to investigate whether Cys-67-82 APC had a potential to improve the outcome of ATIS in this model. Since ex vivo data suggest that the neuroprotective activity is not impaired by Cys-67-82 APC, we hypothesized that Cys-67-82 APC treatment of ATIS in mice could produce measurable benefits due to its potential cytoprotective effect. Cys-67-82 APC may offer an alternative to the treatment of stroke with WT APC or tPA, both of which can cause bleeding in human patients. WT APC has not yet been evaluated in stroke, likely because it impairs hemostasis and therefore would not be useful for the treatment of human ATIS. tPA has been approved for the treatment of stroke but it has severe bleeding side effects, thus its use is severely limited. A safe but equally effective neuroprotective agent, such as Cys-67-82 APC, could be effective in stroke without the danger of increasing intracerebral hemorrhage (ICH).

Negative controls included no treatment and vehicle treatment. Positive controls included two groups of tPA treatments. Three types of APC treatments were evaluated: WT APC, Cys-67-82 APC, and the protein C activator (PCA) double mutant thrombin W215A/E217A which activates endogenous protein C. Each agent was administered at a single dose level between 15 and 60 min of MCAO. The foreign body (filament) was removed from the MCA after 60 min. 30 min later (at 90 min) the LDF probe was removed, anesthesia was terminated, and the animals were observed for one day, when their performance was evaluated. (Table 2).

TABLE 2

Effect of tPA and APC treatments on various outcome parameters of acute thrombotic ischemic stroke in mice.

| Treatment | Dose and Administration | N animals that survived surgery and MCAO | Mortality between 2 and 24 hours after MCAO | Hemorrhage macroscopic evidence of bleeding on autopsy | Infarct % ipsilateral hemisphere mean | Edema % ipsilateral hemisphere mean ± SEM | Neuroscore; performance score at sacrifice, mean | Reperfusion % blood flow recovery 15 min after MCAO mean |
|---|---|---|---|---|---|---|---|---|
| None | — | 10 | 3/13. | 0/13 | 60.0 ± 6.8 | 11.4 ± 1.2 | 3.5 | ND |
| Vehicle | Vehicle (saline), slow iv bolus at 15 min, 100 µL | 10 | 2/12. | 0/12. | 58 ± 5.6 | 9 ± 1.9 | 4 | 47 ± 3 |

TABLE 2-continued

Effect of tPA and APC treatments on various outcome parameters of acute thrombotic ischemic stroke in mice.

| Treatment | Dose and Administration | N animals that survived surgery and MCAO | Mortality between 2 and 24 hours after MCAO | Hemorrhage macroscopic evidence of bleeding on autopsy | Infarct % ipsilateral hemisphere mean | Edema % ipsilateral hemisphere mean ± SEM | Neuroscore; performance score at sacrifice, mean | Reperfusion % blood flow recovery 15 min after MCAO mean |
|---|---|---|---|---|---|---|---|---|
| Protein C activator (PCA; recombinant human W215A/E217A; WE) | 25 µg/kg; 5 min iv bolus at 15 min, 100 µL | 10 | 4/14. | 2/14. | 22.1 ± 6.1 | 7.8 ± 1.4 | 1.5 | 76 ± 4 |
| Plasminogen activator (PA; recombinant human tissue-type PA; tPA) | 2.5 mg/kg; 5 min iv bolus at 15 min post MCAO, 65 µL | 10 | 6/16. | 7/16. | 33.0 ± 10.7 | 5.8 ± 3.2 | 3 | 78 ± 4 |
| Plasminogen activator (recombinant human tPA) | 10 mg/kg/hr; 45 min infusion 15 to 60 min during MCAO, 185 µL | 10 | 3/13. | 4/13. | 15.9 ± 4.9 | 6.7 ± 1.1 | 2 | 81 ± 6 |
| Activated Protein C (human, plasma-derived) | 2.0 mg/kg slow iv bolus at 15 min, 100 µL | 5 | 3/8 | 2/9 | 13.6 ± 7.1 | 6.1 ± 2.5 | 2.5 | 78 ± 8 |
| Cys-Cys Activated Protein C (recombinant human Arg67Cys/Asp82Cys APC) | 2.0 mg/kg slow iv bolus at 15 min, 100 µL | 5 | 1/6 | 2/6 | 26.1 ± 5.3 | 5.9 ± 1.3 | 2.7 | 69 ± 7 |

The animals were sacrificed after neurological evaluation by removal of their blood and perfusion of the circulation with heparinized saline through cardiac puncture (left ventricle) under anesthesia. The brain was cut into coronal sections, visually inspected for hemorrhage (i.e., residual blood in the cranium after saline perfusion), stained with 2% triphenyl-tetrazolium chloride (TTC) and the infarct volumes determined. Other areas, including the surgical sites were also evaluated for hemorrhage.

The data indicates that Cys-67-82 APC treatment during focal cerebral ischemia improved the short term (24 h) neurological outcome of ATIS in mice. Most dramatic is a reduction on mortality (⅙), which was equivalent to mice that received control vehicle alone. Cys-67-82 APC scored higher than any positive controls except plasminogen activator in the neurological performance test. Surrogate markers of stroke, such as infarct volume, seemed to be consistent with the neurological findings. Overall, Cys-67-82 APC had beneficial effects in this model similar to other forms of APC treatment, and as in comparison to tPA, which is the current treatment of choice in humans.

All publications and patents cited in this specification are hereby incorporated by reference in their entirety. The discussion of the references herein is intended merely to summarize the assertions made by the authors and no admission is made that any reference constitutes prior art. Applicants reserve the right to challenge the accuracy and pertinence of the cited references.

What is claimed:

1. A recombinant polypeptide comprising SEQ ID NO: 2.

2. A recombinant protein consisting of two polypeptides, the two polypeptides consisting essentially of the sequence set forth by residues 43-197 of SEQ ID NO: 2 and the sequence set forth by residues 200-461 of SEQ ID NO: 2.

3. A recombinant protein consisting of two polypeptides, the two polypeptides consisting essentially of the sequence set forth by residues 43-197 of SEQ ID NO: 2 and the sequence set forth by residues 212-461 of SEQ ID NO: 2.

4. A recombinant protein produced by proteolytic processing of a sequence having at least 95% identity to SEQ ID NO.1 and having cysteine residues at positions 264 and 279,
   wherein said recombinant protein consists of two polypeptides consisting essentially of the sequence analogous to residues 43-197 of SEQ ID NO: 1 and the sequence analogous to residues 212-461 of SEQ ID NO: 1,
   wherein the recombinant protein has anti-inflammatory activity and reduced anticoagulant activity, compared to the protein consisting essentially of the two polypeptides set forth by residues 43-197 and residues 212-461 of SEQ ID NO: 1.

5. A recombinant protein produced by proteolytic processing of a sequence having at least 95% identity to SEQ ID NO.1 and having cysteine residues at positions 264 and 279,
   wherein said recombinant protein consists of two polypeptides consisting essentially of the sequence analogous to residues 43-197 of SEQ ID NO: 1 and the sequence analogous to residues 200-461 of SEQ ID NO: 1, and
   wherein the recombinant protein has more rapid proteolytic activation to the protein consisting of the two polypeptides consisting essentially of the sequence analogous to residues 43-197 of SEQ ID NO: 1 and the sequence analogous to residues 212-461 of SEQ ID NO: 1, compared to proteolytic activation of the protein consisting essentially of the two polypeptides set forth by residues 43-197 and residues 200-461 of SEQ ID NO: 1 to the protein consisting essentially of the two polypeptides set forth by residues 43-197 and residues 212-461 of SEQ ID NO: 1.

6. A recombinant protein with at least 95% identity to SEQ ID NO.1 and having cysteine residues at positions 264 and 279,
   wherein proteolytic processing of said recombinant protein produces a protein consisting of two polypeptides consisting essentially of the sequence analogous to residues 43-197 of SEQ ID NO: 1 and the sequence analogous to residues 212-461 of SEQ ID NO: 1, and
   wherein the two polypeptide protein has anti-inflammatory activity and reduced anticoagulant activity, compared to the protein consisting essentially of the two polypeptides set forth by residues 43-197 and residues 212-461 of SEQ ID NO: 1.

7. A recombinant polypeptide having at least 95% identity to SEQ ID NO:1 and having cysteine residues at positions 264 and 279.

8. The recombinant polypeptide of claim 1, wherein the cysteine at position 264 and the cysteine at position 279 form a disulfide bond.

9. The recombinant polypeptide of claim 2, wherein the cysteine at position 264 and the cysteine at position 279 form a disulfide bond.

10. The recombinant polypeptide of claim 3, wherein the cysteine at position 264 and the cysteine at position 279 form a disulfide bond.

11. The recombinant polypeptide of claim 4, wherein the cysteine at position 264 and the cysteine at position 279 form a disulfide bond.

12. The recombinant polypeptide of claim 5, wherein the cysteine at position 264 and the cysteine at position 279 form a disulfide bond.

13. The recombinant polypeptide of claim 6, wherein the cysteine at position 264 and the cysteine at position 279 form a disulfide bond.

14. The recombinant polypeptide of claim 7, wherein the cysteine at position 264 and the cysteine at position 279 form a disulfide bond.

15. A composition comprising the recombinant polypeptide of any one of claim 1-3, 4-13, or 14 in a pharmaceutically acceptable formulation.

* * * * *

SEQUENCE LISTING

```
<160> NUMBER OF SEQ ID NOS: 8

<210> SEQ ID NO 1
<211> LENGTH: 461
<212> TYPE: PRT
<213> ORGANISM: Homo sapiens

<400> SEQUENCE: 1

Met Trp Gln Leu Thr Ser Leu Leu Phe Val Ala Thr Trp Gly Ile
1               5                   10                  15

Ser Gly Thr Pro Ala Pro Leu Asp Ser Val Phe Ser Ser Ser Glu Arg
            20                  25                  30

Ala His Gln Val Leu Arg Ile Arg Lys Arg Ala Asn Ser Phe Leu Glu
        35                  40                  45

Glu Leu Arg His Ser Ser Leu Glu Arg Glu Cys Ile Glu Glu Ile Cys
    50                  55                  60
```

```
Asp Phe Glu Glu Ala Lys Glu Ile Phe Gln Asn Val Asp Asp Thr Leu
 65                  70                  75                  80

Ala Phe Trp Ser Lys His Val Asp Gly Asp Gln Cys Leu Val Leu Pro
             85                  90                  95

Leu Glu His Pro Cys Ala Ser Leu Cys Cys Gly His Gly Thr Cys Ile
            100                 105                 110

Asp Gly Ile Gly Ser Phe Ser Cys Asp Cys Arg Ser Gly Trp Glu Gly
        115                 120                 125

Arg Phe Cys Gln Arg Glu Val Ser Phe Leu Asn Cys Ser Leu Asp Asn
130                 135                 140

Gly Gly Cys Thr His Tyr Cys Leu Glu Glu Val Gly Trp Arg Arg Cys
145                 150                 155                 160

Ser Cys Ala Pro Gly Tyr Lys Leu Gly Asp Asp Leu Leu Gln Cys His
                165                 170                 175

Pro Ala Val Lys Phe Pro Cys Gly Arg Pro Trp Lys Arg Met Glu Lys
            180                 185                 190

Lys Arg Ser His Leu Lys Arg Asp Thr Glu Asp Gln Glu Asp Gln Val
            195                 200                 205

Asp Pro Arg Leu Ile Asp Gly Lys Met Thr Arg Arg Gly Asp Ser Pro
210                 215                 220

Trp Gln Val Val Leu Leu Asp Ser Lys Lys Lys Leu Ala Cys Gly Ala
225                 230                 235                 240

Val Leu Ile His Pro Ser Trp Val Leu Thr Ala Ala His Cys Met Asp
                245                 250                 255

Glu Ser Lys Lys Leu Leu Val Arg Leu Gly Glu Tyr Asp Leu Arg Arg
            260                 265                 270

Trp Glu Lys Trp Glu Leu Asp Leu Asp Ile Lys Glu Val Phe Val His
            275                 280                 285

Pro Asn Tyr Ser Lys Ser Thr Thr Asp Asn Asp Ile Ala Leu Leu His
            290                 295                 300

Leu Ala Gln Pro Ala Thr Leu Ser Gln Thr Ile Val Pro Ile Cys Leu
305                 310                 315                 320

Pro Asp Ser Gly Leu Ala Glu Arg Glu Leu Asn Gln Ala Gly Gln Glu
                325                 330                 335

Thr Leu Val Thr Gly Trp Gly Tyr His Ser Ser Arg Glu Lys Glu Ala
            340                 345                 350

Lys Arg Asn Arg Thr Phe Val Leu Asn Phe Ile Lys Ile Pro Val Val
            355                 360                 365

Pro His Asn Glu Cys Ser Glu Val Met Ser Asn Met Val Ser Glu Asn
370                 375                 380

Met Leu Cys Ala Gly Ile Leu Gly Asp Arg Gln Asp Ala Cys Glu Gly
385                 390                 395                 400

Asp Ser Gly Gly Pro Met Val Ala Ser Phe His Gly Thr Trp Phe Leu
                405                 410                 415

Val Gly Leu Val Ser Trp Gly Glu Gly Cys Gly Leu Leu His Asn Tyr
            420                 425                 430

Gly Val Tyr Thr Lys Val Ser Arg Tyr Leu Asp Trp Ile His Gly His
            435                 440                 445

Ile Arg Asp Lys Glu Ala Pro Gln Lys Ser Trp Ala Pro
450                 455                 460

<210> SEQ ID NO 2
<211> LENGTH: 461
<212> TYPE: PRT
```

<213> ORGANISM: Homo sapiens

<400> SEQUENCE: 2

```
Met Trp Gln Leu Thr Ser Leu Leu Phe Val Ala Thr Trp Gly Ile
1               5                   10                  15

Ser Gly Thr Pro Ala Pro Leu Asp Ser Val Phe Ser Ser Glu Arg
                20                  25                  30

Ala His Gln Val Leu Arg Ile Arg Lys Arg Ala Asn Ser Phe Leu Glu
            35                  40                  45

Glu Leu Arg His Ser Ser Leu Glu Arg Glu Cys Ile Glu Glu Ile Cys
        50                  55                  60

Asp Phe Glu Glu Ala Lys Glu Ile Phe Gln Asn Val Asp Asp Thr Leu
65                  70                  75                  80

Ala Phe Trp Ser Lys His Val Asp Gly Asp Gln Cys Leu Val Leu Pro
                85                  90                  95

Leu Glu His Pro Cys Ala Ser Leu Cys Cys Gly His Gly Thr Cys Ile
                100                 105                 110

Asp Gly Ile Gly Ser Phe Ser Cys Asp Cys Arg Ser Gly Trp Glu Gly
            115                 120                 125

Arg Phe Cys Gln Arg Glu Val Ser Phe Leu Asn Cys Ser Leu Asp Asn
130                 135                 140

Gly Gly Cys Thr His Tyr Cys Leu Glu Glu Val Gly Trp Arg Arg Cys
145                 150                 155                 160

Ser Cys Ala Pro Gly Tyr Lys Leu Gly Asp Asp Leu Leu Gln Cys His
                165                 170                 175

Pro Ala Val Lys Phe Pro Cys Gly Arg Pro Trp Lys Arg Met Glu Lys
                180                 185                 190

Lys Arg Ser His Leu Lys Arg Asp Thr Glu Asp Gln Glu Asp Gln Val
            195                 200                 205

Asp Pro Arg Leu Ile Asp Gly Lys Met Thr Arg Arg Gly Asp Ser Pro
210                 215                 220

Trp Gln Val Val Leu Leu Asp Ser Lys Lys Lys Leu Ala Cys Gly Ala
225                 230                 235                 240

Val Leu Ile His Pro Ser Trp Val Leu Thr Ala Ala His Cys Met Asp
                245                 250                 255

Glu Ser Lys Lys Leu Leu Val Cys Leu Gly Glu Tyr Asp Leu Arg Arg
                260                 265                 270

Trp Glu Lys Trp Glu Leu Cys Leu Asp Ile Lys Glu Val Phe Val His
            275                 280                 285

Pro Asn Tyr Ser Lys Ser Thr Thr Asp Asn Asp Ile Ala Leu Leu His
290                 295                 300

Leu Ala Gln Pro Ala Thr Leu Ser Gln Thr Ile Val Pro Ile Cys Leu
305                 310                 315                 320

Pro Asp Ser Gly Leu Ala Glu Arg Glu Leu Asn Gln Ala Gly Gln Glu
                325                 330                 335

Thr Leu Val Thr Gly Trp Gly Tyr His Ser Ser Arg Glu Lys Glu Ala
                340                 345                 350

Lys Arg Asn Arg Thr Phe Val Leu Asn Phe Ile Lys Ile Pro Val Val
            355                 360                 365

Pro His Asn Glu Cys Ser Glu Val Met Ser Asn Met Val Ser Glu Asn
                370                 375                 380

Met Leu Cys Ala Gly Ile Leu Gly Asp Arg Gln Asp Ala Cys Glu Gly
385                 390                 395                 400
```

```
Asp Ser Gly Gly Pro Met Val Ala Ser Phe His Gly Thr Trp Phe Leu
            405                 410                 415

Val Gly Leu Val Ser Trp Gly Glu Gly Cys Gly Leu Leu His Asn Tyr
        420                 425                 430

Gly Val Tyr Thr Lys Val Ser Arg Tyr Leu Asp Trp Ile His Gly His
        435                 440                 445

Ile Arg Asp Lys Glu Ala Pro Gln Lys Ser Trp Ala Pro
    450                 455                 460

<210> SEQ ID NO 3
<211> LENGTH: 33
<212> TYPE: DNA
<213> ORGANISM: Homo sapiens

<400> SEQUENCE: 3
aagaagctcc ttgtctgcct tggagagtat gac                               33

<210> SEQ ID NO 4
<211> LENGTH: 33
<212> TYPE: DNA
<213> ORGANISM: Homo sapiens

<400> SEQUENCE: 4
gtcatactct ccaaggcaga caaggagctt ctt                               33

<210> SEQ ID NO 5
<211> LENGTH: 33
<212> TYPE: DNA
<213> ORGANISM: Homo sapiens

<400> SEQUENCE: 5
gagaagtggg agctgtgcct ggacatcaag gag                               33

<210> SEQ ID NO 6
<211> LENGTH: 33
<212> TYPE: DNA
<213> ORGANISM: Homo sapiens

<400> SEQUENCE: 6
ctccttgatg tccaggcaca gctcccactt ctc                               33

<210> SEQ ID NO 7
<211> LENGTH: 1776
<212> TYPE: DNA
<213> ORGANISM: Homo sapiens

<400> SEQUENCE: 7
gctgtcatgg cggcaggacg gcgaacttgc agtatctcca cgacccgccc ctacaggtgc    60
cagtgcctcc agaatgtggc agctcacaag cctcctgctg ttcgtggcca cctgggaat    120 ttccggcaca ccagctcctc ttgactcagt gttctccagc agcgagcgtg cccaccaggt   180
gctgcggatc cgcaaacgtg ccaactcctt cctggaggag ctccgtcaca gcagcctgga   240
gcgggagtgc atagaggaga tctgtgactt cgaggaggcc aaggaaattt tccaaaatgt   300
ggatgacaca ctggccttct ggtccaagca cgtcgacggt gaccagtgct tggtcttgcc   360
cttggagcac ccgtgcgcca gcctgtgctg cgggcacggc acgtgcatcg acggcatcgg   420
cagcttcagc tgcgactgcc gcagcggctg ggagggccgc ttctgccagc gcgaggtgag   480
cttcctcaat tgctcgctgg acaacggcgg ctgcacgcat tactgcctag aggaggtggg   540
ctggcggcgc tgtagctgtg cgcctggcta caagctgggg gacgacctcc tgcagtgtca   600
```

```
cccngcagtg aagttcccct gtgggaggcc ctggaagcgg atggagaaga agcgcagtca    660
cctgaaacga gacacagaag accaagaaga ccaagtagat ccgcggctca ttgatgggaa    720
gatgaccagg cggggagaca gcccctggca ggtggtcctg ctggactcaa agaagaagct    780
ggcctgcggg gcagtgctca tccacccctc ctgggtgctg acagcggccc actgcatgga    840
tgagtccaag aagctccttg tcaggcttgg agagtatgac ctgcggcgct gggagaagtg    900
ggagctggac ctggacatca aggaggtctt cgtccacccc aactacagca agagcaccac    960
cgacaatgac atcgcactgc tgcacctggc ccagcccgcc accctctcgc agaccatagt   1020
gcccatctgc tcccggaca gcggccttgc agagcgcgag ctcaatcagg ccggccagga   1080
gaccctcgtg acgggctggg gctaccacag cagccgagag aaggaggcca agagaaaccg   1140
caccttcgtc ctcaacttca tcaagattcc cgtggtcccg cacaatgagt gcagcgaggt   1200
catgagcaac atggtgtctg agaacatgct gtgtgcgggc atcctcgggg accggcagga   1260
tgcctgcgag ggcgacagtg gggggcccat ggtcgcctcc ttccacggca cctggttcct   1320
ggtgggcctg gtgagctggg gtgagggctg tgggctcctt cacaactacg gcgtttacac   1380
caaagtcagc cgctacctcg actggatcca tgggcacatc agagacaagg aagcccccca   1440
gaagagctgg gcaccttagc gaccctccct gcagggctgg gcttttgcat ggcaatggat   1500
gggacattaa agggacatgt aacaagcaca ccggcctgct gttctgtcct ccatccctc   1560
tttggggctc ttctggaggg aagtaacatt tactgagcac ctgttgtatg tcacatgcct   1620
tatgaataga atcttaactc ctagagcaac tctgtggggt ggggaggagc agatccaagt   1680
tttgcggggt ctaaagctgt gtgtgttgag ggggatactc tgtttatgaa aagaataaa    1740
aaacacaacc acgaaaaaaa aaaaaaaaaa aaaaaa                             1776

<210> SEQ ID NO 8
<211> LENGTH: 1776
<212> TYPE: DNA
<213> ORGANISM: Homo sapiens

<400> SEQUENCE: 8
gctgtcatgg cggcaggacg gcgaacttgc agtatctcca cgacccgccc ctacaggtgc     60
cagtgcctcc agaatgtggc agctcacaag cctcctgctg ttcgtggcca cctggggaat    120
ttccggcaca ccagctcctc ttgactcagt gttctccagc agcgagcgtg cccaccaggt    180
gctgcggatc cgcaaacgtg ccaactcctt cctggaggag ctccgtcaca gcagcctgga    240
gcgggagtgc atagaggaga tctgtgactt cgaggaggcc aaggaaattt ccaaaatgt    300
ggatgacaca ctggccttct ggtccaagca cgtcgacggt gaccagtgct tggtcttgcc    360
cttggagcac ccgtgcgcca gctgtgctg cgggacggc acgtgcatcg acggcatcgg    420
cagcttcagc tgcgactgcc gcagcggctg ggagggccgc ttctgccagc gcgaggtgag    480
cttcctcaat tgctcgctgg acaacggcgg ctgcacgcat tactgcctag aggaggtggg    540
ctggcggcgc tgtagctgtg cgcctggcta caagctgggg gacgacctcc tgcagtgtca    600
ccccgcagtg aagttcccct tgtgggaggcc ctggaagcgg atggagaaga agcgcagtca    660
cctgaaacga gacacagaag accaagaaga ccaagtagat ccgcggctca ttgatgggaa    720
gatgaccagg cggggagaca gcccctggca ggtggtcctg ctggactcaa agaagaagct    780
```

```
ggcctgcggg gcagtgctca tccacccctc ctgggtgctg acagcggccc actgcatgga      840
tgagtccaag aagctccttg tctgccttgg agagtatgac ctgcggcgct gggagaagtg      900
ggagctgtgc ctggacatca aggaggtctt cgtccacccc aactacagca agagcaccac      960
cgacaatgac atcgcactgc tgcacctggc ccagcccgcc accctctcgc agaccatagt     1020
gcccatctgc ctcccggaca gcggccttgc agagcgcgag ctcaatcagg ccggccagga     1080
gaccctcgtg acgggctggg gctaccacag cagccgagag aaggaggcca agagaaaccg     1140
caccttcgtc ctcaacttca tcaagattcc cgtggtcccg cacaatgagt gcagcgaggt     1200
catgagcaac atggtgtctg agaacatgct gtgtgcgggc atcctcgggg accggcagga     1260
tgcctgcgag ggcgacagtg gggggcccat ggtcgcctcc ttccacggca cctggttcct     1320
ggtgggcctg gtgagctggg gtgagggctg tgggctcctt cacaactacg gcgtttacac     1380
caaagtcagc cgctacctcg actggatcca tgggcacatc agagacaagg aagcccccca     1440
gaagagctgg gcaccttagc gaccctccct gcagggctgg gcttttgcat ggcaatggat     1500
gggacattaa agggacatgt aacaagcaca ccggcctgct gttctgtcct tccatccctc     1560
ttttgggctc ttctggaggg aagtaacatt tactgagcac ctgttgtatg tcacatgcct     1620
tatgaataga atcttaactc ctagagcaac tctgtggggt ggggaggagc agatccaagt     1680
tttgcggggt ctaaagctgt gtgtgttgag ggggatactc tgtttatgaa aaagaataaa     1740
aaacacaacc acgaaaaaaa aaaaaaaaaa aaaaaa                               1776
```